(12) United States Patent
Kay et al.

(10) Patent No.: US 8,034,922 B2
(45) Date of Patent: Oct. 11, 2011

(54) COMPOSITIONS AND METHODS FOR MODULATING ACTIVITY OF CAPPED SMALL RNAS

(75) Inventors: Mark A. Kay, Los Altos, CA (US); Dirk Haussecker, Buehlertal (DE); Dan Cao, Mountain View, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 12/545,729

(22) Filed: Aug. 21, 2009

(65) Prior Publication Data

US 2010/0069464 A1  Mar. 18, 2010

Related U.S. Application Data

(60) Provisional application No. 61/091,170, filed on Aug. 22, 2008.

(51) Int. Cl.
  *C07H 21/04* (2006.01)
  *A61K 31/70* (2006.01)
(52) U.S. Cl. ......................................... 536/24.5; 514/44
(58) Field of Classification Search ......................... None
  See application file for complete search history.

(56) References Cited

U.S. PATENT DOCUMENTS

| | | | |
|---|---|---|---|
| 5,580,767 A * | 12/1996 | Cowsert et al. | 435/375 |
| 2004/0127446 A1* | 7/2004 | Blatt et al. | 514/44 |
| 2006/0063731 A1 | 3/2006 | Lewis et al. | |
| 2006/0240093 A1 | 10/2006 | Maclachlan et al. | |
| 2006/0240451 A1* | 10/2006 | Jendrisak et al. | 435/6 |
| 2007/0027099 A1 | 2/2007 | Lin et al. | |

OTHER PUBLICATIONS

Haussecker et al. Nature Structural & Molecular Biology 2008, vol. 15, pp. 714-721.*
Chang, J. and Taylor, J.M., "Susceptibility of human hepatitis delta virus RNAs to small interfering RNA action", *Journal of Virology*, 77(17):9728-9731 (2003).
Radhakrishnan, S.K. et al., "RNA interference as a new strategy against viral hepatitis" *Proc Natl Acad Sci U S A*, 323(2):173-181 (2004).
Taylor, J.A. and Naoumov, N., "The potential of RNA interference as a tool in the management of viral hepatitis", *Journal of Hepatology*, 42:139-144 (2005).

* cited by examiner

*Primary Examiner* — Tracy Vivlemore
(74) *Attorney, Agent, or Firm* — Judy M. Mohr; Susan J. Myers Fitch; King & Spalding LLP

(57) ABSTRACT

Compositions and methods for modulating transcription by RNA polymerases are described.

9 Claims, 10 Drawing Sheets

SEQUENCE LISTING

```
<160> NUMBER OF SEQ ID NOS: 37

<210> SEQ ID NO 1
<211> LENGTH: 18
<212> TYPE: DNA
<213> ORGANISM: Artificial Sequence
<220> FEATURE:
<223> OTHER INFORMATION: Synthetic oligonucleotide probe for HDV small
      RNA

<400> SEQUENCE: 1
gtcctcagta ctcttact                                                   18

<210> SEQ ID NO 2
<211> LENGTH: 28
<212> TYPE: DNA
<213> ORGANISM: Artificial Sequence
<220> FEATURE:
<223> OTHER INFORMATION: Synthetic oligonucleotide probe for
      antigenomic pode, bottom strand

<400> SEQUENCE: 2
ggcggcagtc ctcagtactc ttactctt                                        28

<210> SEQ ID NO 3
<211> LENGTH: 21
<212> TYPE: DNA
<213> ORGANISM: Artificial Sequence
<220> FEATURE:
<223> OTHER INFORMATION: Synthetic oligonucleotide probe for miR-15a1

<400> SEQUENCE: 3
acaaaccatt atgtgctgct a                                               21
```

<210> SEQ ID NO 4
<211> LENGTH: 22
<212> TYPE: DNA
<213> ORGANISM: Artificial Sequence
<220> FEATURE:
<223> OTHER INFORMATION: Synthetic oligonucleotide probe for let-7a1

<400> SEQUENCE: 4
aactatacaa cctactacct ca                                        22

<210> SEQ ID NO 5
<211> LENGTH: 22
<212> TYPE: DNA
<213> ORGANISM: Artificial Sequence
<220> FEATURE:
<223> OTHER INFORMATION: Synthetic oligonucleotide probe for antigenomic
      antipode top strand

<400> SEQUENCE: 5
gaatcgagag aaaagtggct ct                                        22

<210> SEQ ID NO 6
<211> LENGTH: 24
<212> TYPE: DNA
<213> ORGANISM: Artificial Sequence
<220> FEATURE:
<223> OTHER INFORMATION: Synthetic oligonucleotide probe for antigenomic
      antipode, top strand

<400> SEQUENCE: 6
acccacaaat ctctctctag attc                                      24

<210> SEQ ID NO 7
<211> LENGTH: 22
<212> TYPE: DNA
<213> ORGANISM: Artificial Sequence
<220> FEATURE:
<223> OTHER INFORMATION: Synthetic oligonucleotide probe for genomic
      antipode, top strand

<400> SEQUENCE: 7
gaatctagag agatttgtgg gt                                        22

<210> SEQ ID NO 8
<211> LENGTH: 22
<212> TYPE: DNA
<213> ORGANISM: Artificial Sequence
<220> FEATURE:
<223> OTHER INFORMATION: Synthetic oligonucleotide probe for genomic
      antipode, bottom strand

<400> SEQUENCE: 8
agagccactt ttctctcgat tc                                        22

<210> SEQ ID NO 9
<211> LENGTH: 28
<212> TYPE: DNA
<213> ORGANISM: Artificial Sequence
<220> FEATURE:
<223> OTHER INFORMATION: Synthetic oligonucleotide probe for antigenomic
      pode, top strand

<400> SEQUENCE: 9
taaagaggag actgctggac tcgccgcc                                  28

<210> SEQ ID NO 10

```
<211> LENGTH: 28
<212> TYPE: DNA
<213> ORGANISM: Artificial Sequence
<220> FEATURE:
<223> OTHER INFORMATION: Synthetic oligonucleotide probe for genomic
      pode, top strand

<400> SEQUENCE: 10
aagagtaaga gtactgagga ctgccgcc                                           28

<210> SEQ ID NO 11
<211> LENGTH: 25
<212> TYPE: DNA
<213> ORGANISM: Artificial Sequence
<220> FEATURE:
<223> OTHER INFORMATION: Synthetic oligonucleotide probe for genomic
      pode, bottom strand

<400> SEQUENCE: 11
gcggcgagtc cagcagtctc ctctt                                              25

<210> SEQ ID NO 12
<211> LENGTH: 28
<212> TYPE: DNA
<213> ORGANISM: Artificial Sequence
<220> FEATURE:
<223> OTHER INFORMATION: Synthetic oligonucleotide T4 PNK end-labelled
      probe

<400> SEQUENCE: 12
ggcggcagtc ctcagtactc ttactctt                                           28

<210> SEQ ID NO 13
<211> LENGTH: 16
<212> TYPE: DNA
<213> ORGANISM: Artificial Sequence
<220> FEATURE:
<223> OTHER INFORMATION: Synthetic PE-small oligonucleotide primer

<400> SEQUENCE: 13
gcggcagtcc tcagta                                                        16

<210> SEQ ID NO 14
<211> LENGTH: 19
<212> TYPE: DNA
<213> ORGANISM: Artificial Sequence
<220> FEATURE:
<223> OTHER INFORMATION: Synthetic PE-NegControl oligonucleotide primer

<400> SEQUENCE: 14
gactcggacc ggctcatct                                                     19

<210> SEQ ID NO 15
<211> LENGTH: 23
<212> TYPE: DNA
<213> ORGANISM: Artificial Sequence
<220> FEATURE:
<223> OTHER INFORMATION: Synthetic Hybrid-F1 oligonucleotide primer

<400> SEQUENCE: 15
gagtaagagt actgaggact gcc                                                23

<210> SEQ ID NO 16
<211> LENGTH: 20
<212> TYPE: DNA
<213> ORGANISM: Artificial Sequence
<220> FEATURE:
<223> OTHER INFORMATION: Synthetic Hybrid-F2 oligonucleotide primer
```

```
<400> SEQUENCE: 16
acagaaaaga gtaagagtac                                              20

<210> SEQ ID NO 17
<211> LENGTH: 19
<212> TYPE: DNA
<213> ORGANISM: Artificial Sequence
<220> FEATURE:
<223> OTHER INFORMATION: Synthetic Hybrid-F3 oligonucleotide primer

<400> SEQUENCE: 17
cggcgagtcc agcagtctc                                               19

<210> SEQ ID NO 18
<211> LENGTH: 20
<212> TYPE: DNA
<213> ORGANISM: Artificial Sequence
<220> FEATURE:
<223> OTHER INFORMATION: Synthetic Hybrid-R oligonucleotide primer

<400> SEQUENCE: 18
cccgcgtctc ctcgctcgga                                              20

<210> SEQ ID NO 19
<211> LENGTH: 20
<212> TYPE: DNA
<213> ORGANISM: Artificial Sequence
<220> FEATURE:
<223> OTHER INFORMATION: Synthetic Hybrid RT-R oligonucleotide primer

<400> SEQUENCE: 19
tgacatcccc tctcgggagc                                              20

<210> SEQ ID NO 20
<211> LENGTH: 19
<212> TYPE: DNA
<213> ORGANISM: Artificial Sequence
<220> FEATURE:
<223> OTHER INFORMATION: Synthetic Hybrid-F oligonucleotide primer

<400> SEQUENCE: 20
tctgtaaaga ggagactgc                                               19

<210> SEQ ID NO 21
<211> LENGTH: 20
<212> TYPE: DNA
<213> ORGANISM: Artificial Sequence
<220> FEATURE:
<223> OTHER INFORMATION: Synthetic Hybrid-R oligonucleotide primer

<400> SEQUENCE: 21
tacctccatc tggtccgttc                                              20

<210> SEQ ID NO 22
<211> LENGTH: 20
<212> TYPE: DNA
<213> ORGANISM: Artificial Sequence
<220> FEATURE:
<223> OTHER INFORMATION: Synthetic Hybrid RT-R oligonucleotide primer

<400> SEQUENCE: 22
cctcttccta ggtccggagt                                              20

<210> SEQ ID NO 23
<211> LENGTH: 22
```

```
<212> TYPE: DNA
<213> ORGANISM: Artificial Sequence
<220> FEATURE:
<223> OTHER INFORMATION: Synthetic Hybrid-F oligonucleotide primer

<400> SEQUENCE: 23
tctatcggaa tctagagaga tt                                              22

<210> SEQ ID NO 24
<211> LENGTH: 20
<212> TYPE: DNA
<213> ORGANISM: Artificial Sequence
<220> FEATURE:
<223> OTHER INFORMATION: Synthetic Hybrid-R oligonucleotide primer

<400> SEQUENCE: 24
tcgaccccag tgaataaagc                                                 20

<210> SEQ ID NO 25
<211> LENGTH: 20
<212> TYPE: DNA
<213> ORGANISM: Artificial Sequence
<220> FEATURE:
<223> OTHER INFORMATION: Synthetic Hybrid RT-R oligonucleotide primer

<400> SEQUENCE: 25
atactcttcc cagccgatcc                                                 20

<210> SEQ ID NO 26
<211> LENGTH: 19
<212> TYPE: DNA
<213> ORGANISM: Artificial Sequence
<220> FEATURE:
<223> OTHER INFORMATION: Synthetic Hybrid-R oligonucleotide primer

<400> SEQUENCE: 26
cgatagagaa tcgagagaa                                                  19

<210> SEQ ID NO 27
<211> LENGTH: 19
<212> TYPE: DNA
<213> ORGANISM: Artificial Sequence
<220> FEATURE:
<223> OTHER INFORMATION: Synthetic Hybrid-R oligonucleotide primer

<400> SEQUENCE: 27 gaccccttc gaaagtgac                                                   19

<210> SEQ ID NO 28
<211> LENGTH: 21
<212> TYPE: DNA
<213> ORGANISM: Artificial Sequence
<220> FEATURE:
<223> OTHER INFORMATION: Synthetic Hybrid-RT-R oligonucleotide primer

<400> SEQUENCE: 28
aaggggacga gtgaggctta t                                               21

<210> SEQ ID NO 29
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 29
atgagccggt ccgagtcgag gaa                                             23
```

```
<210> SEQ ID NO 30
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 30
atgagccggt ccgagtagta gga                                            23

<210> SEQ ID NO 31
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 31
cataggatat act                                                       13

<210> SEQ ID NO 32
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 32
caatgatgat at                                                        12

<210> SEQ ID NO 33
<211> LENGTH: 23
<212> TYPE: DNA
<213> ORGANISM: Artificial Sequence
<220> FEATURE:
<223> OTHER INFORMATION: Synthetic hepatitis delta virus oligonucleotide

<400> SEQUENCE: 33
taagagtact gaggactgcc gcc                                            23

<210> SEQ ID NO 34
<211> LENGTH: 22
<212> TYPE: DNA
<213> ORGANISM: Artificial Sequence
<220> FEATURE:
<223> OTHER INFORMATION: Synthetic hepatitis delta virus oligonucleotide

<400> SEQUENCE: 34
aagagtactg aggactgccg cc                                             22

<210> SEQ ID NO 35
<211> LENGTH: 25
<212> TYPE: DNA
<213> ORGANISM: Artificial Sequence
<220> FEATURE:
<223> OTHER INFORMATION: Synthetic inhibitor polynucleotide

<400> SEQUENCE: 35
ggcggcagtc ctcagtactc ttact                                          25

<210> SEQ ID NO 36
<211> LENGTH: 23
<212> TYPE: DNA
<213> ORGANISM: Artificial Sequence
<220> FEATURE:
<223> OTHER INFORMATION: Synthetic inhibitor polynucleotide
```

```
<400> SEQUENCE: 36
ggcggcagtc ctcagtactc tta                                        23

<210> SEQ ID NO 37
<211> LENGTH: 22
<212> TYPE: DNA
<213> ORGANISM: Artificial Sequence
<220> FEATURE:
<223> OTHER INFORMATION: Synthetic inhibitor polynucleotide

<400> SEQUENCE: 37
ggcggcagtc ctcagtactc tt                                         22
```

COMPOSITIONS AND METHODS FOR MODULATING ACTIVITY OF CAPPED SMALL RNAS

CROSS-REFERENCE TO RELATED APPLICATIONS

This application claims priority to U.S. Provisional Application Ser. No. 61/091,170, filed on 22 Aug. 2008, which is incorporated herein by reference in its entirety.

STATEMENT REGARDING GOVERNMENT INTEREST

This invention was made with government support under contracts AI 071068 and DK 078424 awarded by the National Institutes of Health (NIH). Accordingly, the United States government has certain rights in this invention.

FIELD OF THE INVENTION

The present compositions and methods are for modulating interactions involving nucleic acids, particularly relating to transcription by RNA polymerases.

REFERENCE TO SEQUENCE LISTING, TABLE OR COMPUTER PROGRAM

A "Sequence Listing" is submitted with this application in the form of a paper copy and a text file created 20 Aug. 2009 and named "586008253US00seq.txt" (6981 bytes), the contents of which are incorporated herein by reference in their entirety.

BACKGROUND

RNA polymerases are nucleotidyl transferase enzymes that produce RNA by polymerizing ribonucleotides at the 3' end of an RNA transcript. In cells, RNA polymerases are needed for constructing RNA chains from DNA or RNA templates, a process called transcription. Control of the process of transcription affects patterns of gene expression and thereby allows a cell to adapt to a changing environment, perform specialized roles within an organism, and maintain basic metabolic processes necessary for survival. Therefore, it is hardly surprising that the activity of RNA polymerases is both complex and highly regulated. Examples of products of RNA polymerases include messenger RNA (mRNA), non-coding RNAs such as transfer RNA (tRNA) and ribosomal RNA (rRNA), microRNA (miRNA), and catalytic RNAs such as ribozymes.

RNA polymerases are essential to life and are found in all organisms and many viruses. Of the RNA polymerases in eukaryotes, RNA Polymerase I (also called Pol I) is the enzyme that transcribes ribosomal RNA (excluding 5S rRNA, which is synthesized by RNA Polymerase III), which accounts for over 50% of the total RNA synthesized in a cell. RNA polymerase II (also called RNAP II and Pol II) catalyzes the transcription of DNA to synthesize precursors of mRNA and most snRNA and microRNA. A 550 kDa complex of 12 subunits, RNAP II is the most-studied type of RNA polymerase. A wide range of transcription factors are required for RNAP II to bind to its promoters and begin transcription. RNA polymerase III (also called Pol III) transcribes DNA to synthesize ribosomal 5S rRNA, tRNA and other small RNAs. The genes transcribed by RNA Pol III fall in the category of "housekeeping" genes whose expression is required in all cell types and most environmental conditions. Thus, the regulation of Pol III transcription is primarily tied to the regulation of cell growth and the cell cycle, requiring fewer regulatory proteins than RNA polymerase II.

RNA polymerases can initiate transcription at specific DNA sequences known as promoters, producing an RNA chain complementary to the template DNA strand. The process of adding nucleotides to the RNA strand is known as elongation. In eukaryotes, RNA polymerases can build chains millions of nucleotides in length. RNA polymerases will preferentially release the RNA transcript at specific DNA sequences encoded at the end of genes known as terminators.

Many viruses also encode RNA polymerases. Perhaps the most widely studied viral RNA polymerase is found in bacteriophage T7. The single-subunit T7 RNA polymerase is related to that found in mitochondria and chloroplasts, and shares considerable homology to DNA polymerase. It is believed that most viral polymerases therefore evolved from DNA polymerase and are not directly related to the multi-subunit polymerases described above.

Viral polymerases are diverse, and include some forms which can use RNA as a template instead of DNA. This occurs in negative strand RNA viruses and dsRNA viruses, both of which exist for a portion of their life cycle as double-stranded RNA. However, some positive strand RNA viruses, such as polio, also contain these RNA-dependent RNA polymerases.

RNA-directed transcription refers to transcription from an RNA template and is carried out by an RNA-dependent RNA polymerase (RdRP). RNA-directed transcription occurs in RNAi-mediated gene silencing in non-vertebrate organisms such as *C. elegans*, fungi, and plants (Wassenegger, M. and Krczal, G. *Trends Plant Sci.* 11:142-51 (2006)). RNA-directed transcription is also part of the normal replication cycle of a number of vertebrate RNA viruses. All these examples of RNA-directed transcription involve a dedicated RdRP. In the case of virus replication, the RdRP is virally encoded.

Hepatitis Delta Virus (HDV) is the smallest known animal virus and encodes only one protein, the Hepatitis Delta Antigen (HDAg). HDAg is required for viral replication, but does not have polymerase activity. HDV is naturally acquired either by co-infection with Hepatitis B Virus (HBV) or by super-infection of a host with an existing HBV infection. The role of HBV in the natural HDV life-cycle relates to the Hepatitis B surface antigen (HBsAg) which forms part of the HDV envelope and is responsible for hepatocyte-specific infection. However, once inside essentially any mammalian cell, HDV replication is independent of HBV, so long as HDV RNA and a source of HDAg are provided.

Following infection, the HDV RNA-HDAg ribonucleoprotein particle (RNP) is recruited to the nucleus where the circular genomic HDV RNA serves as a template for rolling-circle replication, thereby generating multimers of antigenomic HDV RNAs. As HDV does not encode a protein with polymerase activity, virus genome replication relies on host RNA polymerases (Taylor, J. M. *Curr. Top. Microbiol. Immunol.* 307:1-23 (2006)). The multimers of antigenomic HDV RNAs are cleaved into monomers by a ribozyme activity in the antigenomic RNA, which then circularises by end-ligation. The resulting antigenomic monomers then become templates for analogous rolling-circle transcription, thereby yielding more circular genomic HDV RNAs. Due to the presence of >70% intramolecular Watson-Crick base-pair complementarity, both genomic and antigenomic HDV RNA assume a compact, unbranched rod-like structure.

In addition to being the template for antigenomic RNA synthesis, genomic HDV RNA also serves as the template for transcription of HDAg mRNA. This mRNA is capped and polyadenylated as is typical for RNA Polymerase II (Pol II) transcripts (Hsieh, S. Y. et al. *J. Virol.* 64:3192-8 (1990); Gudima, S. et al. *J. Virol.* 74:7204-10 (2000). For this reason, and the additional observation that both genomic and antigenomic HDV RNA can be immunoprecipitated with Pol II antibodies (Greco-Stewart, V. S. et al. *Virology* 357:68-78 (2007)), it appears that the Pol II core enzyme mediates HDV RNA-directed transcription. However, the mechanism behind HDV replication and transcription remains poorly understood.

SUMMARY

The following aspects and embodiments thereof described and illustrated below are meant to be exemplary and illustrative, not limiting in scope.

In one aspect, a small priming RNA (spRNA) molecule having a 5' cap and an ability to prime transcription by RNA polymerases is provided. A 5' cap RNA is defined here as an RNA with a 5' end of 7-methylguanosine (7mG) as found on most mRNAs or 2,2,7-trimethylguanosine (TMG) as found on many snRNAs. In another aspect, an spRNA is provided that has an ability to prime transcription by RNA polymerases, but may have a non-cap 5' end. In some embodiments, said spRNA molecule has a sequence with at least about 80% identity to SEQ ID NO: 33 or SEQ ID NO: 34. In some embodiments, the sequence has at least about 90% identity to SEQ ID NO: 33 or SEQ ID NO: 34. In some embodiments, the sequence has at least 95% identity to SEQ ID NO: 33 or SEQ ID NO: 34. In particular embodiments, the spRNA molecule has the sequence of SEQ ID NO: 33 or SEQ ID NO: 34.

In one aspect, a method for modulating transcription by an RNA polymerase in a cell is provided, comprising delivering to the cell a compound effective to modulate the biogenesis or activity of an spRNA.

In another aspect, a method for inhibiting replication of HDV is provided, comprising providing a compound effective to bind to or inhibit the activity of the spRNA molecule. In some embodiments, the compound comprises a nucleic acid. In particular embodiments, the nucleic acid has the sequence selected from the group consisting of SEQ ID NO. 1 and SEQ ID NO. 35-37. In some embodiments, the compound comprises a small molecule.

In a related aspect, a method for identifying a therapeutic agent capable of inhibiting replication of HDV is provided, comprising contacting the spRNA molecule with a candidate therapeutic agent and evaluating ability of the candidate agent to inhibit replication of HDV. In some embodiments, the compound is an antisense nucleic acid or an RNAi agent having RNAi-like processing and silencing activity (e.g., a short-interfering RNA (siRNA), microRNA (miRNA) or short-hairpin RNA (shRNA)).

In another aspect, an antisense nucleic acid or an RNAi agent capable of hybridizing to the spRNA molecule is provided.

In yet another aspect, a system comprising the spRNA molecule is provided, the system being capable of replicating genomic HDV.

In another aspect, a method for modulating spRNA-primed transcription in a cell is provided, comprising delivering to the cell a nucleic acid or small molecule that modulates the interaction between a short RNA involved in RNA-directed transcription and a target viral or cellular nucleic acid. In some embodiments, the short RNA has the sequence of SEQ ID NOs: 33 or 34. In some embodiments, the target viral or cellular nucleic acid is RNA. In some embodiments, the target viral or cellular nucleic acid is HDV genomic or antigenomic RNA. In some embodiments, the target viral or cellular nucleic acid is DNA.

In another aspect, a nucleic acid or small molecule which modulates spRNA-primed transcription in a cell is provided. In some embodiments, the modulation is a decrease in transcription. In some embodiments, the modulation is an increase in transcription.

In another aspect, a method for modulating the generation of the spRNA by RNA polymerases is provided. In some embodiments, an enzyme involved in biogenesis of the spRNA is contacted with a small molecule such that the amount or rate of biogenesis of the spRNA is increased or decreased. In another embodiment, the activity of an enzyme involved in capping the spRNA is modulated by targeting it with an siRNA, antisense oligonucleotide or similar nucleic acid reagent.

In addition to the exemplary aspects and embodiments described above, further aspects and embodiments will become apparent by reference to the drawings and by study of the following descriptions.

BRIEF DESCRIPTION OF THE DRAWINGS

FIG. 3A shows the results of a β-elimination assay, in which the mobility of the HDV small RNA increases following β-elimination. FIGS. 3B and 3C show the results of enzymatic analysis of the 5' end of HDV small RNA.

FIG. 4A shows the presence or absence of the small RNA in nuclear and cytoplasmic cell fractions. FIG. 4B shows the presence or absence of antigenomic and genomic RNA in nuclear and cytoplasmic cell fractions. FIG. 4C shows the presence of the HDV small RNA in HDV virions.

FIG. 5A illustrates the primer combinations tested and whether a hybrid product was obtained. The relative positions of primers and their polarity are indicated by the arrows. The sequence of the HDV small RNA is indicated in bold text.

DETAILED DESCRIPTION

I. Introduction

Described are compositions and methods for modulating RNA-directed transcription in mammalian cells. The compositions and methods are based, in part, on the discovery of a small, 5'-capped RNA that directs the transcription of a mRNA from a viral RNA genome. This small RNA represents a novel target for pharmaceutical compositions and method designed to reduce RNA-mediated transcription in virus infected cells, thereby treating or preventing viral infections. The small RNA also represents a target for pharmaceutical compositions for modulating cellular RNA-mediated transcription associated with diseases, disorders, or other conditions affecting mammalian subjects.

Historically, a 5' cap was believed to occur primarily on precursor mRNAs and a few other primary RNA transcripts found in eukaryotes. The process of 5' capping results in a mature messenger RNA which is then able to undergo translation. The enzymes for capping were believed to bind to RNA polymerase II exclusively, ensuring specificity to mRNA transcripts. Capping also ensures the messenger RNA's stability while it undergoes translation in the process of protein synthesis, and is a highly regulated process which occurs in the cell nucleus.

Applicants were the first to discover small, 5'-capped priming RNAs that direct transcription by a non-viral RNA polymerase in mammalian cells. With this discovery, Applicants envisage that small, 5'-capped priming RNAs may direct transcription by various RNA polymerases, and from either RNA or DNA templates.

These and other features of the present composition and methods are described with reference to the accompanying drawings.

II. Experiments and Observations in Support of the Compositions and Methods

The following experiments relate to Hepatitis Delta Virus (HDV) but are broadly applicable to viral and cellular RNA-mediated transcription.

A. A Small Viral RNA Maps to a Viral mRNA Transcription Initiation Site

Figure 1:
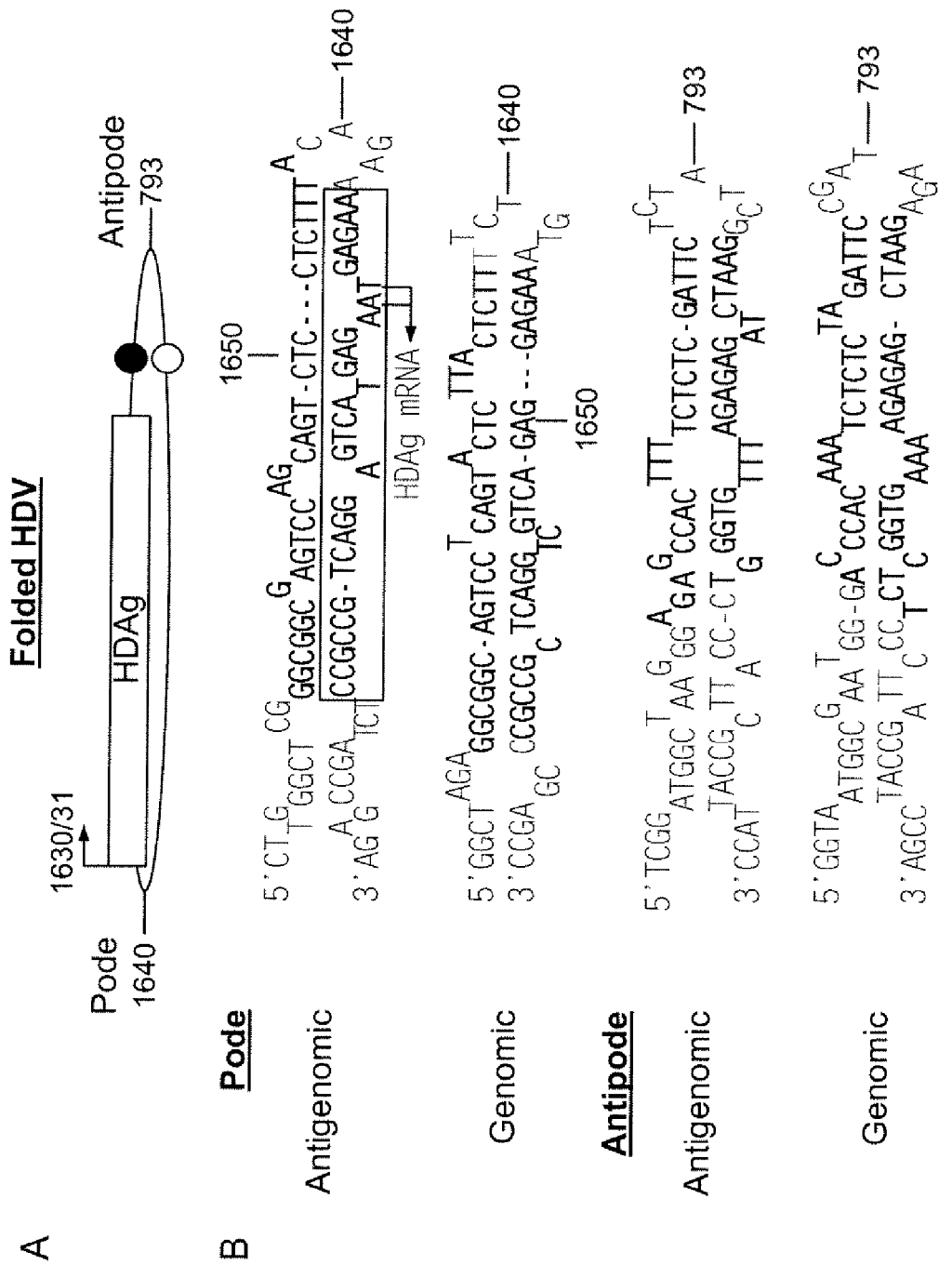
FIG. 1A shows a schematic of the HDV genomic and antigenomic RNA secondary structure. The HDAg mRNA transcriptional start site is indicated by an arrow and ribozymes are indicated by circles. Nucleotide numbering is as described (Kuo, M. Y. et al. J. Virol. 62:1855-61 (1988)).
FIG. 1B shows the predicted secondary structures of the hairpin ends of both genomic and antigenomic RNA. Target sequences for probes are shown in bold text and the region from which the small RNA was detected is shown in a black box. The HDAg mRNA transcriptional start sites is indicated by arrows.
FIG. 1C shows the results of northern blot analysis to identify the HDV small RNA derived from the antigenomic pode.
Figure 1:
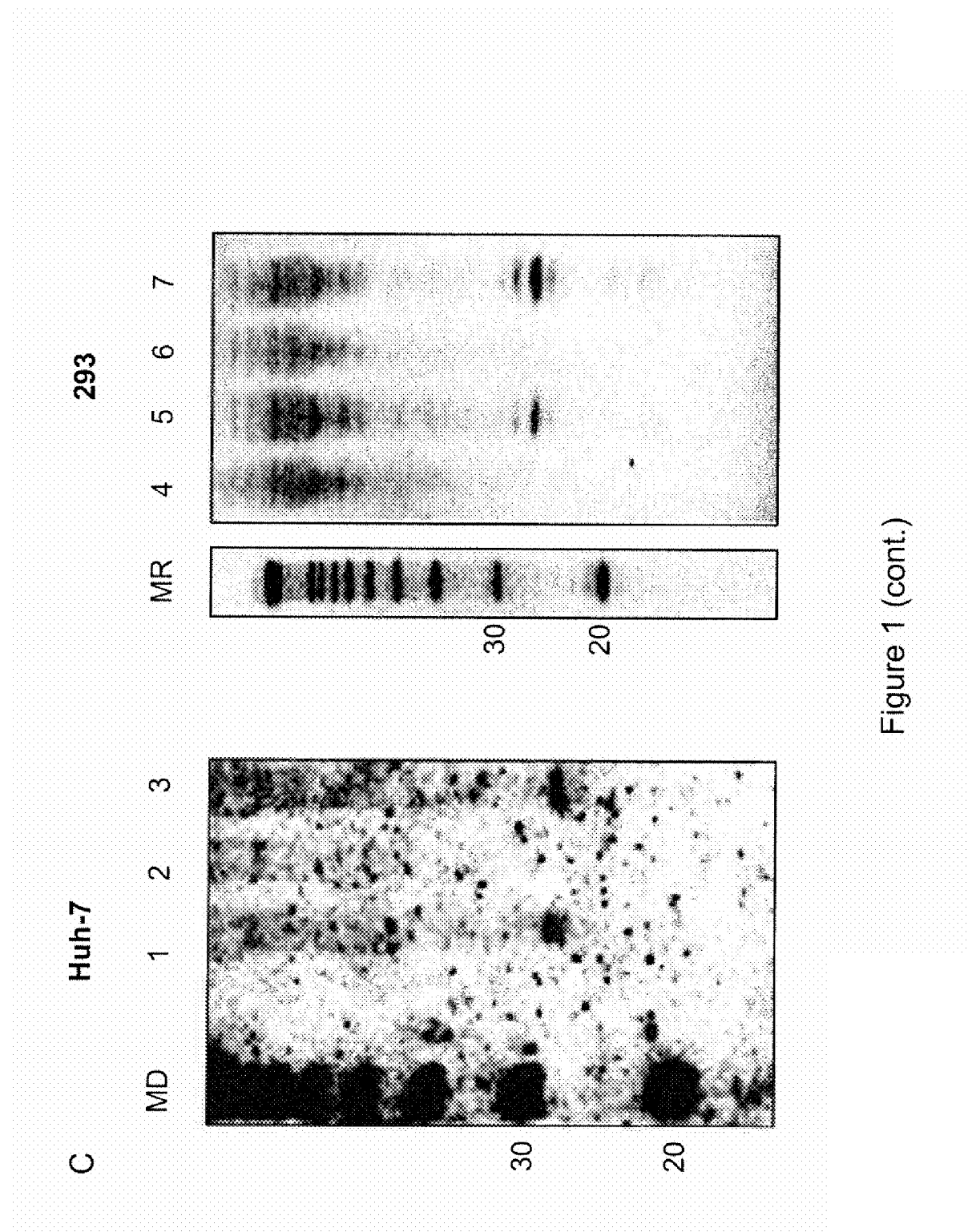

Plasmid DNA or RNA was transfected into mammalian cells to trigger HDV replication in culture, as described in Example 1. The plasmid DNA used for DNA transfections contained 1.2× unit-length antigenomic HDV sequences under the control of a cytomegalovirus (CMV) promoter. In vitro transcribed antigenomic HDV RNA or HDAg mRNA were used for RNA transfections. Due to the pre-microRNA-like appearance of the ends of the rod-structured genomic and the antigenomic HDV RNAs, the hairpin ends were referred to as the 'pode' and 'antipode,' as illustrated in FIG. 1.

Figure 3:
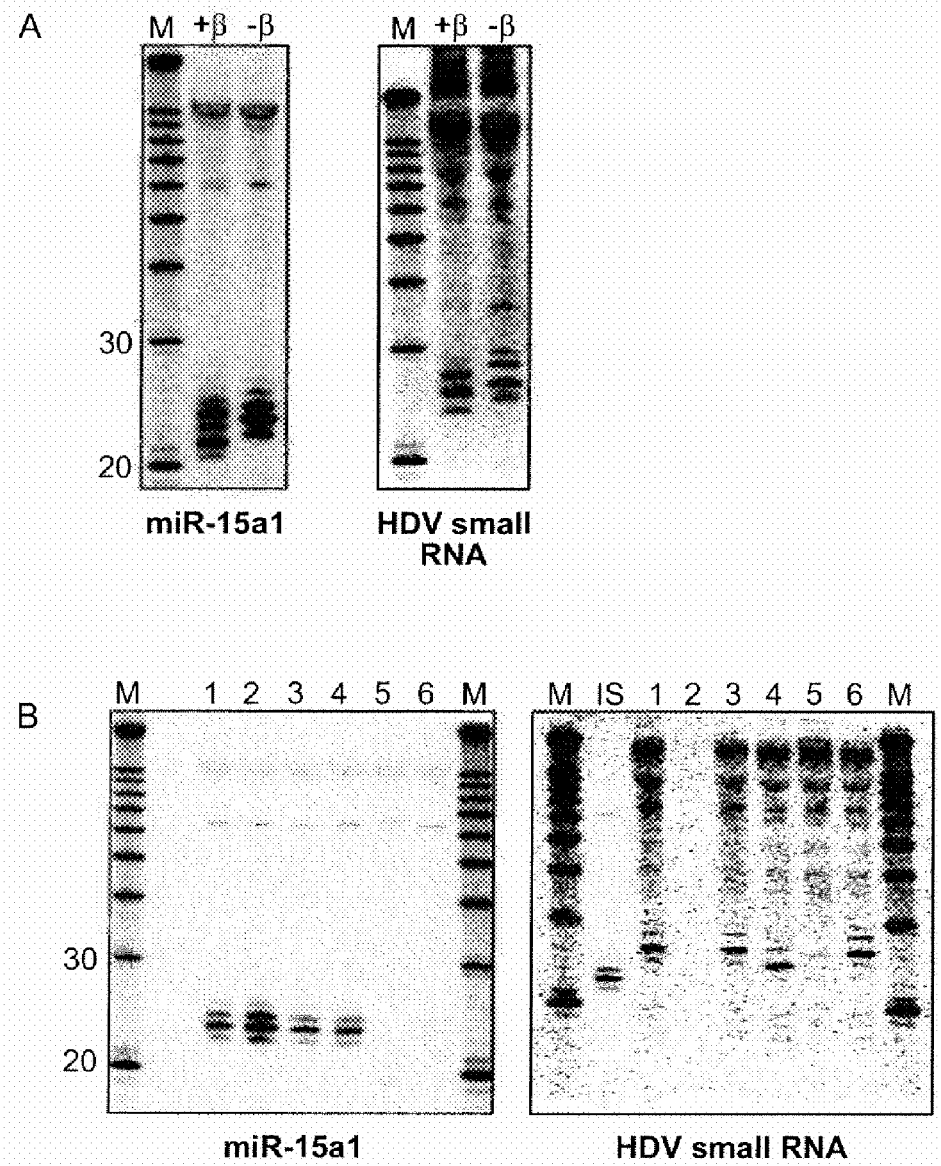
FIGS. 3A-3D show the results of experiments performed to characterize the HDV small RNA.
FIG. 3E shows the predicted structure of the HDV small RNA.
Figure 3:
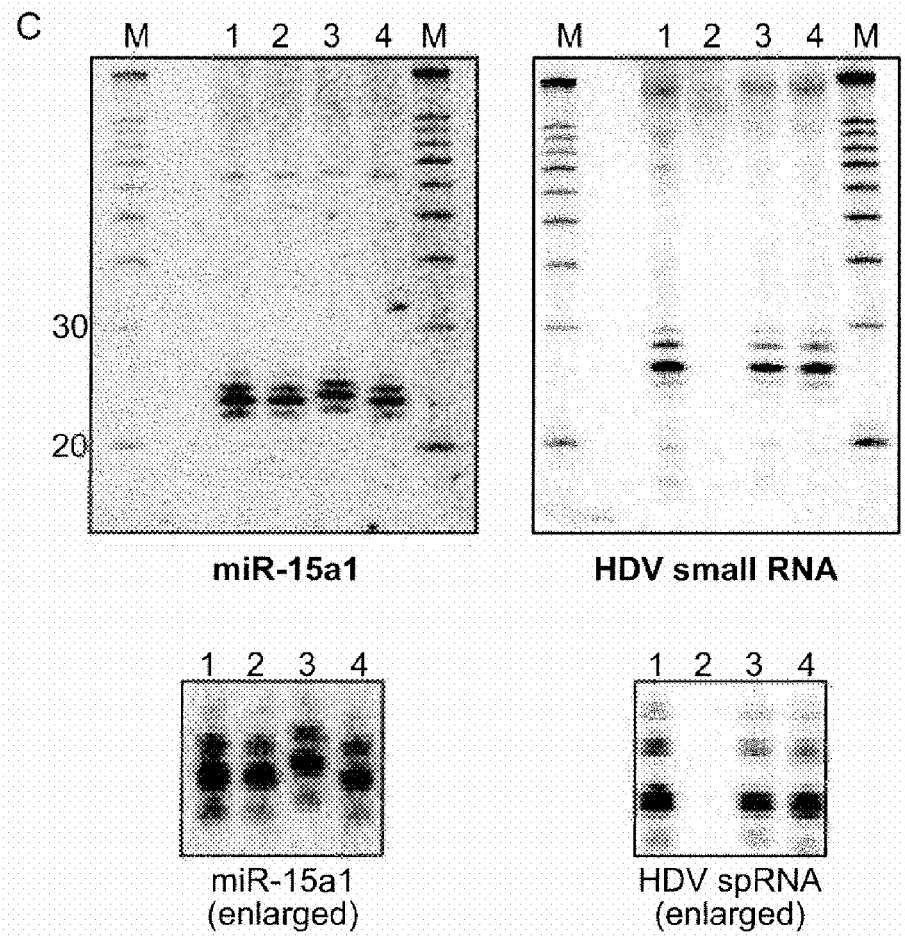
Figure 3:
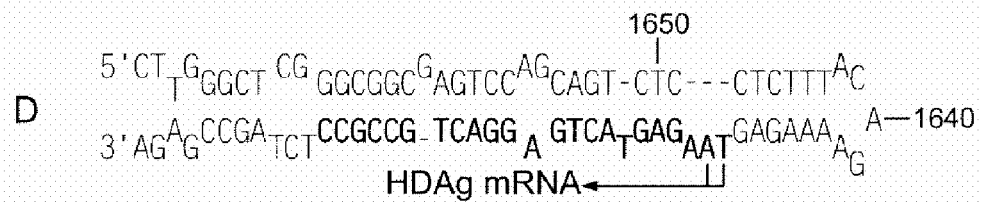
Figure 3:

Oligonucleotide probes/primers for use in northern blot analysis were designed to detect small RNAs corresponding to either the top or bottom strands of these hairpins (FIGS. 1A and 1B and Example 2). Of the eight probes used in the experiment, only the one (SEQ ID NO: 1) that targeted the bottom strand of the antigenomic pode (black box, FIG. 1B) detected an HDV replication-dependent small RNA. This small RNA was observed in both 293 and Huh-7 cells, regardless of whether HDV replication had been induced by plasmid DNA or RNA transfection (FIG. 1C). Transfection with a plasmid containing an early non-sense mutation in HDAg (i.e., DNA induction using mutant/mutated HDAg), which consequently does not support HDV replication (see, e.g., FIG. 4B, lane 1), did not result in the appearance of the small RNA in the cells (FIG. 1C, lanes 2 and 6), demonstrating that the small RNA resulted from HDV replication. Based on the gel mobility of this RNA relative to known microRNAs and its 5' end structure (see FIG. 3), the RNA was estimated to be about 23 nucleotides (nts) in length.

To more precisely map the location of the small RNA with respect to the HCV genome, a primer extension assay was used to detect the 5' end of the small RNA, but not that of the collinear, approximately 800 nucleotide, HDAg mRNA. The 5' end of the HDAg mRNA is the only RNA that has been mapped to positions 1,630 and 1,631 of the genome (Hsieh, S. Y. et al. *J. Virol.* 64:3192-8 (1990); Modahl, L. E. and Lai, M. M. *J. Virol.* 72:5449-56 (1998); Gudima, S. et al. *J. Virol.* 73:6533-9 (1999)). Accordingly, an RNA population depleted of RNAs larger than 200 nucleotides, including HDAg mRNA, was used to refine the analysis. A negative control oligonucleotide primer that hybridized downstream of the predicted HDV was used to distinguish the small RNA and HDAg mRNA.

Figure 2:
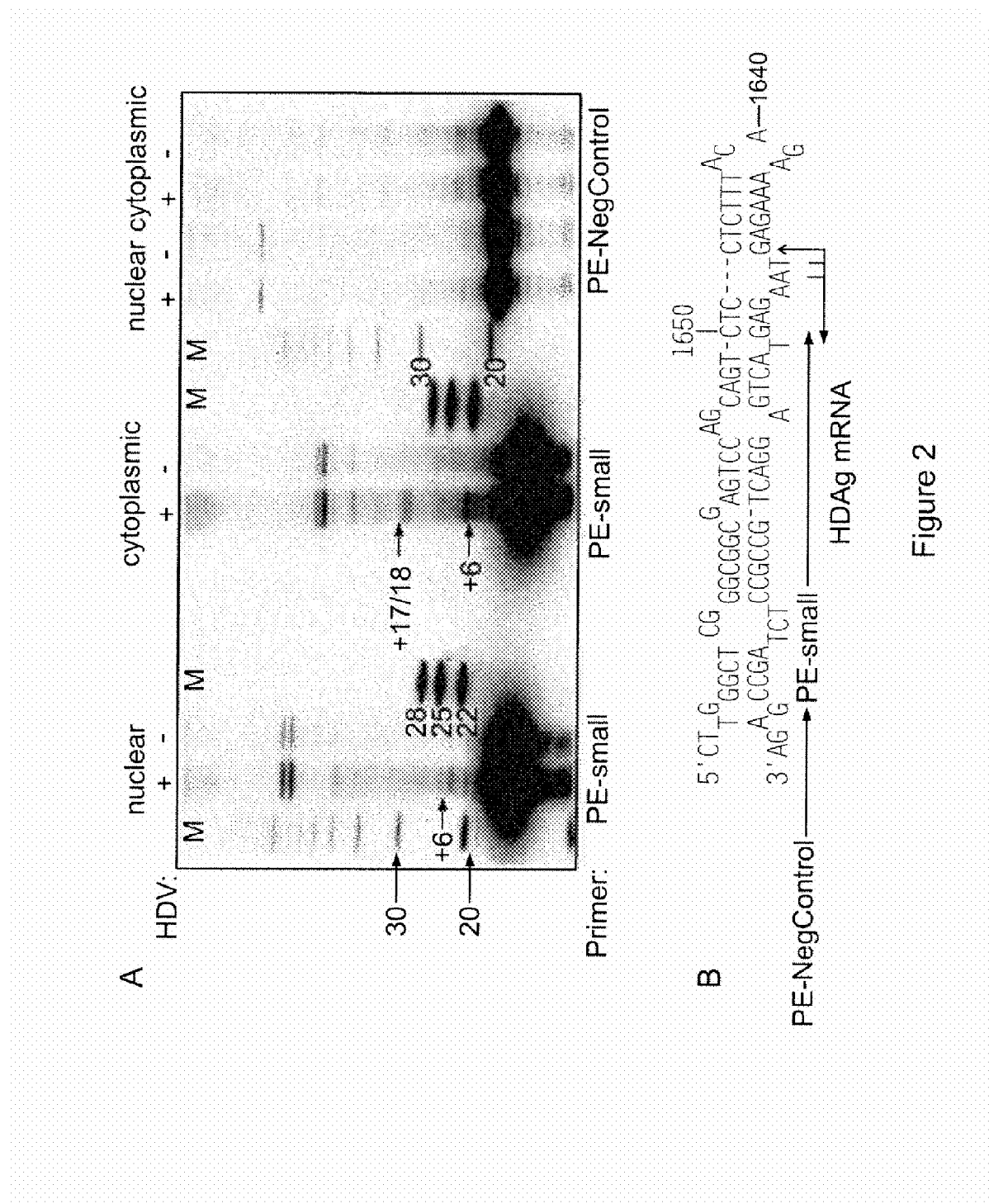
FIG. 2A shows the results of a primer extension assay to map the 5' end of the HDV small RNA present in nuclear and/or cytoplasmic RNA fractions.
FIG. 2B shows that the 5' end of the HDV small RNA maps predominantly to nucleotide position 1,631 (upright arrow). Known HDAg mRNA initiation sites are indicated by arrows pointing to the left.

Initially, a small RNA-specific primer in which the 3' end corresponded to position 1,627 was used to obtain a 3-4 nucleotide extension that was only observed in cells where HDV replication was occurring (data not shown). To confirm the result, a second primer was utilized, which lacked the two 3'-most nucleosides of the first primer, and which produced a 6-nucleotide extension in the presence of RNA from HDV replicating cells (FIG. 2A). Based on such results, the 5' end of the small RNA was mapped to position 1,631, and to a lesser extent position 1,630, which is the known to be the HDAg mRNA initiation site (Hsieh, S. Y. et al. *J. Virol.* 64:3192-8 (1990); Modahl, L. E. and Lai, M. M. *J. Virol.* 72:5449-56 (1998); Gudima, S. et al. *J. Virol.* 73:6533-9 (1999)). No HDV-specific bands were observed with the control primer that hybridized downstream of the predicted HDV small RNA, confirming the efficient depletion of HDAg mRNA in the RNA used for the assay.

Based on such data, it was apparent that the 5' end of the HDV small RNA mapped primarily to position 1,631 (and to a lesser extent 1,630) and ended with the evolutionarily conserved (Beard, M. R. et al. *J. Virol.* 70:4986-95 (1996)) GC-rich box (FIG. 2B), thereby having a nucleotide sequences as shown below. Note that the corresponding region of the genome includes the conserved secondary RNA structure thought to include the HDV promoter (Beard, M. R. et al. *J. Virol.* 70:4986-95 (1996)).

| Sequence (5'→3') | Range (nts) | Length (nts) | SEQ ID NO: |
|---|---|---|---|
| taagagtactgaggactgccgcc | 1,631-1,609 | 23 | 33 |
| aagagtactgaggactgccgcc | 1,630-1,609 | 22 | 34 |

Figure 4:
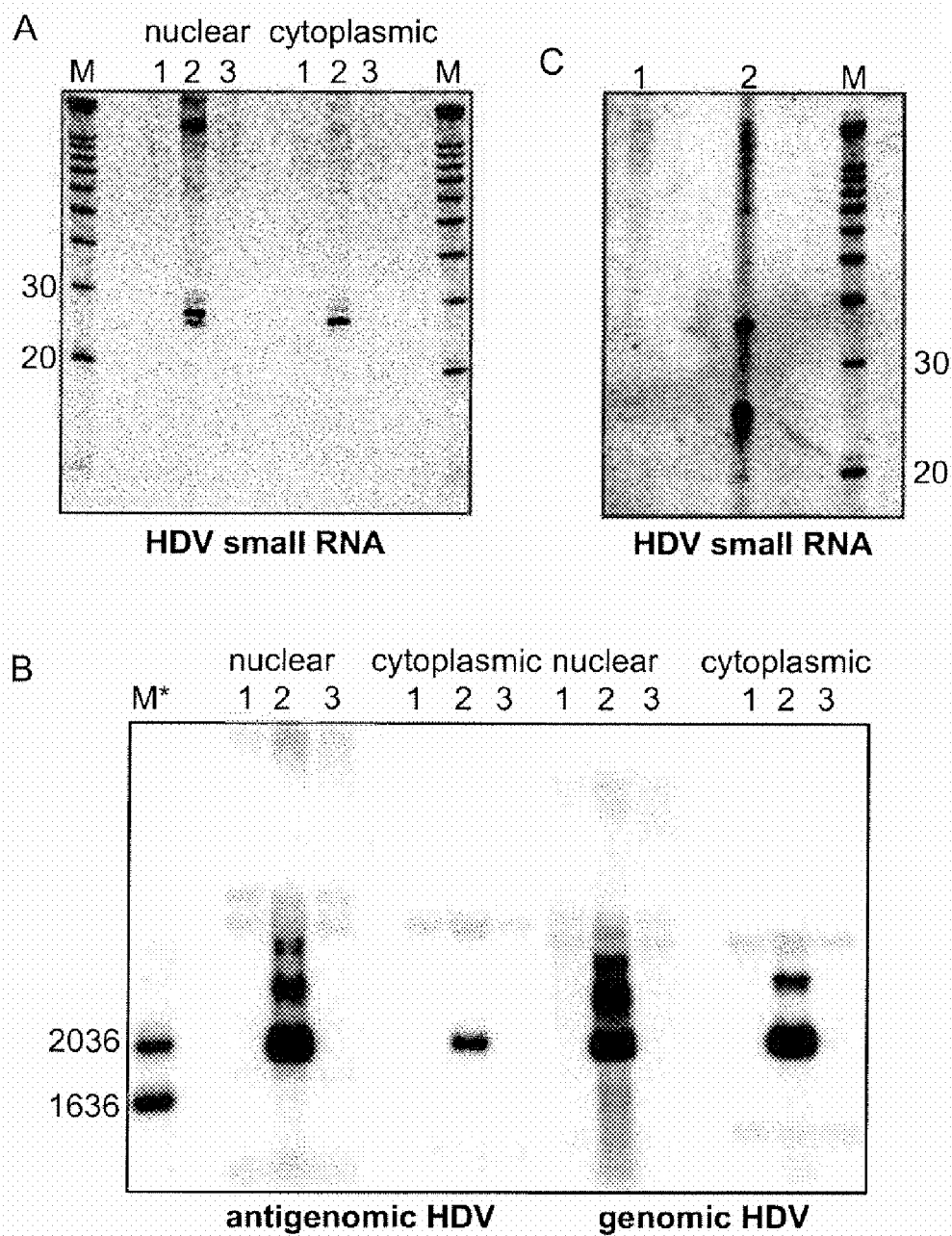
FIGS. 4A-4C show the results of experiments performed to localize the HDV small RNA to various RNA containing cell and virus fractions.

Using RNA from the cytoplasmic fraction in the primer extension assay, an extension product that mapped the 5' end of another cytoplasmic HDV RNA (just beyond the hairpin loop) was identified, in addition to the aforementioned 6-nucleotide extension product. This RNA was only infrequently detected, and only with the PE small primer (SEQ ID NO: 13). This RNA may correspond to another ~35 nucleotide RNA that is part of the HDV virion (FIG. 4C).

Further experiments were performed to determine whether small RNAs within a microRNA-like precursor hairpin could have RNAi-like processing and silencing activity. Previous studies have shown that Drosha is the enzyme that processes primary microRNAs into precursor hairpins, which are then further processed by another RNase, Dicer, into the mature microRNAs (Kim, V. N. Nat. Rev. Mol. Cell. Biol. 6:376-85 (2005)). However, neither Drosha nor Dicer depletion (using RNAi) had an effect on the abundance of the small RNAs or the accumulation of full-length HDV RNA in cells (data not shown), suggesting that the HDV small RNA was not involved in silencing.

Moreover, when luciferase reporter constructs that carried target sequences in their 3' UTR that were complementary to the region from which the HDV small RNA was derived, a HDV replication-dependent decrease in luminescence was not observed (data not shown), further indicating the HDV small RNA was not involved in a silencing role.

B. Role in Pol II Transcription Initiation

That the 5' end of the small RNA coincided with the 5' end of the HDAg mRNA suggested that the small RNA may perform a priming function in HCV genome replication. A β-elimination assay was used to determine whether the 5' and 3' end structures of the small RNA were compatible with a priming function. In this reaction, RNAs such as human microRNA-15a1 (miR-15a1), which have terminal nucleosides with free 2'- and 3'-hydroxyl groups undergo an elimination reaction in which the last nucleoside is lost, leading to an increase in the gel mobility of the RNA (Hutvagner, G. et al. Science 293:834-8 (2001)). This was also the case for the HDV small RNA, suggesting that the RNA performs a priming function (FIG. 3A).

The chemical structure of the 5' end of the small RNA was then analysed by enzymatic means, as shown in FIG. 3B. Here, RNA was treated with various enzymes that modify certain types of 5' ends to produce an affect on gel mobility. For example, T4 Polynucleotide Kinase (PNK) adds a phosphate group to 5' hydroxylated RNAs. However, incubation with PNK did not affect the mobility of the small RNA, excluding the presence of a free 5'-OH group (FIG. 3B, lane 3). This was also the case for miR-15a1 which is known to carry a 5' monophosphate. Another enzyme, tobacco acid pyrophosphatase (TAP) cleaves various pyrophosphate bonds including those in triphosphorylated or methylguanosine-capped RNAs, thereby leaving a 5' monophosphate group. While a change from triphosphate to monophosphate should not visibly affect the mobility of a small RNA on a 20% polyacrylamide gel with a 19:1 ratio of acrylamide:bisacrylamide (Pak, J. and Fire, A. Science 315:241-4 (2007)), the loss of a 7-methyl-guanosine cap structure should lead to a visible increase in mobility. Indeed, the mobility of the HDV small RNA increased following TAP treatment (FIG. 3B, lane 4), while the miR-15a1 RNA was not affected by TAP treatment.

Following incubation with TAP, both the HDV small RNA and the largely 22-nucleotide miR-15a1 carry a 5' monophosphate, allowed a more accurate size comparison. This allowed the size of the small RNA to be estimated at about 23 nucleotides (FIG. 3B, 'IS').

T4 RNA ligase catalyzes the ligation of a 5' phosphoryl-terminated nucleic acid donor to a 3' hydroxyl-terminated nucleic acid acceptor through the formation of a 3'→5' phosphodiester bond. leading to the disappearance of 5' monophosphorylated and 3' hydroxylated small RNAs in Northern blots (Pak, J. and Fire, A. Science 315:241-4 (2007)). In the presence of RNA ligase, both the miR-15a1 RNA and the HDV small RNA disappeared (FIG. 3B, lanes 5), likely due to the ligation of the 3' hydroxyl end of the HDV small RNA to a heterogeneous population of 5' monophosphorylated RNAs.

Finally, the 5' phosphate-dependent terminator exonuclease was used to selectively remove 5' monophosphorylated RNAs. The disappearance of the miR-15a1 5'-phosphorylated microRNA confirmed the activity of the enzyme in the assay; however, the HDV small RNA was unaffected by the enzyme, consistent with the presence of a 5' cap structure (FIG. 3B, lane 6).

The presence of triphosphorylated 5' end on the small RNA was further excluded by treatment with Antarctic phosphatase (AntP), which catalyzes the removal of 5' phosphate groups from DNA and RNA. AntP did not affect the mobility of the HDV small RNA as did subsequent treatment with PNK (FIG. 3C). In contrast, the migration of Mir-15a1 was slightly retarded by AntP treatment and restored to its original mobility by PNK, demonstrating that the Mir-15a1 RNA, but not the HDV small RNA, possessed a triphosphorylated 5' end.

Figure 7:
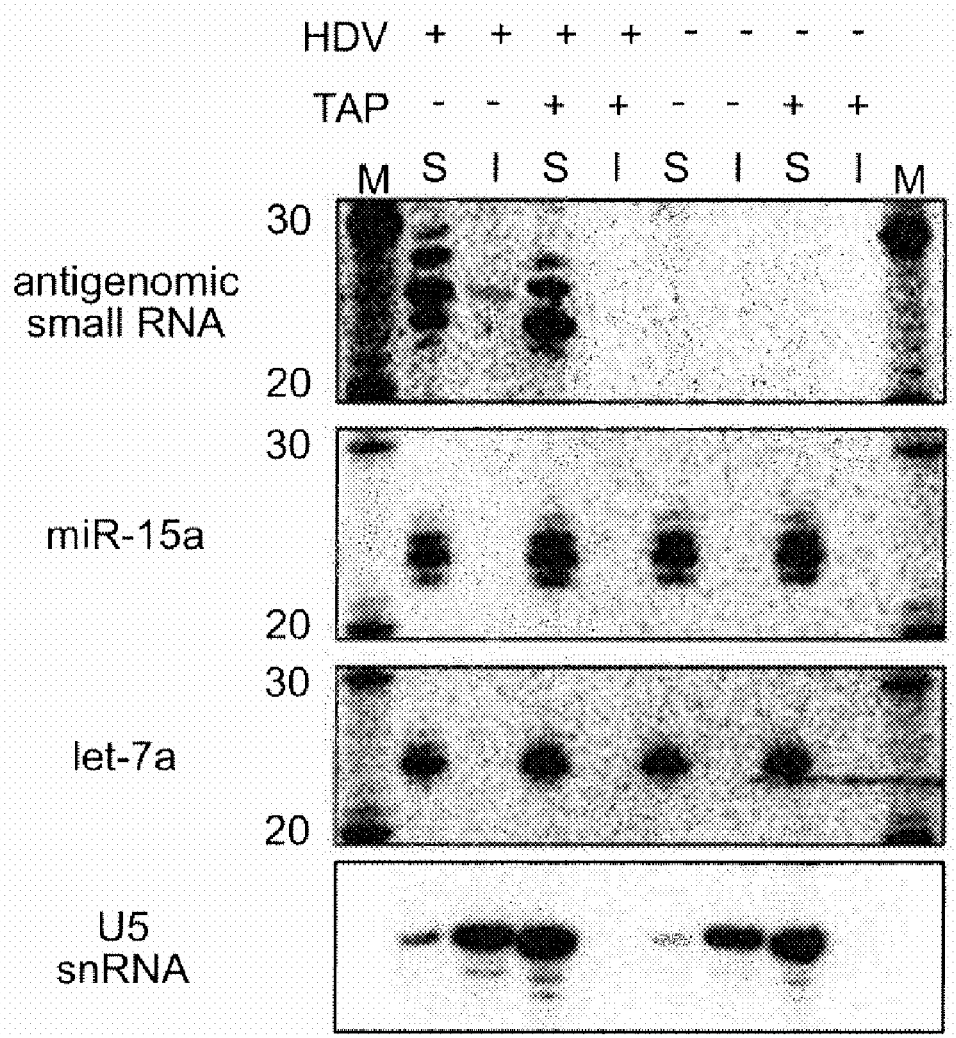
FIG. 7 shows the results of an RNA immunoprecipitation experiment using anti-2,2,7-trimethylguanosine antibody, K121. The immunoprecipitation efficiency of the HDV small RNA, U5 snRNA (positive control), and microRNAs miR-15a and let-7a (negative controls) was analysed by Northern blot. "S": supernatant; "I": IP fraction.

To further investigate the 5' cap structure, an immunoprecipitation was performed with an antibody that efficiently recognizes trimethylguanosine caps as carried by structural RNAs such as U5 snRNA. This antibody is known to also weakly recognize mRNA-like 7-methylguanosine caps. RNAs with other 5' modifications such as microRNAs which carry 5' phosphate groups, are not recognized by the antibody. The intermediate immunoprecipitation efficiency of the HDV small RNA confirmed the mRNA-like 5' cap structure of the HDV small RNA (FIG. 7; Example 7).

Based on these enzymatic analyses and immunoprecipitation experiments, it was apparent that the HDV small RNA possessed an mRNA-like 5' cap. The presence of the cap structure, the behaviour of the small RNA in the 2'-3' hydroxylation reaction, and the coincidence of the 5' end of the small RNA and the HDAg mRNA, pointed towards a function of the HDV small RNA in HDAg mRNA transcription initiation.

C. Co-Localisation of the HDV Small RNA with Genomic HDV RNA

Localisation of the HDV small RNA was further investigated by nuclear-cytoplasmic RNA fractionation. Interestingly, the HDV small RNA, which is of antigenomic polarity (see, e.g., FIG. 1B) was found both in the nucleus and in the cytoplasm (FIG. 4A). In contrast, monomeric and multimeric HDV RNAs of the same antigenomic polarity were largely restricted to the nucleus (FIG. 4B), as expected (Macnaughton, T. B. and Lai, M. M. J. Virol. 76:3928-35 (2002)), consistent with their role as nuclear replication intermediates. This observation further indicates that the cytoplasmic RNA fraction was substantially free from nuclear RNA contaminants. In contrast, genomic HDV RNA, particularly the mature monomeric form, was present in both the nucleus and cytoplasm (FIG. 4B), consistent with genomic HDV-RNP being exported to the cytoplasm and packaged together with HDAg and HBsAg into the HDV virion during a typical infection.

Co-localisation of the antigenomic HDV small RNA with genomic HDV RNA was likely mediated by base-pairing.

One possibility was that, similar to some U-rich RNPs, a cytoplasmic remodelling step is necessary for the activity of the HDV small RNA. As such, it had been shown before in heterokaryon assays that genomic RNPs can shuttle between nuclei (Tavanez, J. P. of al. RNA 8:637-46 (2002)). Alternatively or additionally, antigenomic HDV small RNA may be packaged into the mature virus particle together with genomic HDV RNA so that it may be available as a primer for HDAg mRNA transcription soon after re-infection.

Further localization of the HDV small RNA was performed by isolating RNA from HDV virions produced by co-expressing HBsAg during HDV replication (Sureau, C. at al. *J. Virol.* 67:366-72 (1993)). Substantial amounts of HDV small RNA was detected in the virion RNA sample (FIG. 4C), which was in comparison much greater than the amount of small RNA present in cellular RNA obtaining from cells in which HDV was replicating. Interestingly, a second ~35-nucleotide RNA was detected in the virion RNA sample using the same probe. The presence of HBsAg and virus packaging may be necessary for the stability of this RNA.

D. Identification of an Antigenomic-Genomic HDV RNA Hybrid Related to the 3' End of the HDV Small RNA If the antigenomic HDV small RNA was involved with initiation of genomic HDV RNA transcription, the RNA should at some point possess a free 3' end for the addition of nucleosides before its dissociation from the antigenomic HDV RNA and subsequent annealing to genomic HDV RNA. This suggests the existence of a transient hybrid RNA consisting of a 5' end having antigenomic RNA sequences and a 3' end having genomic HDV RNA sequences. A similar hybrid was detected during the development of an in vitro HDV replication system but was not regarded as being part of normal HDV transcription (Filipovska, J. and Konarska, M. M. *RNA* 6:41-54 (2000)).

The existence of such hybrid RNAs was further investigated using a set of RT-PCR primers in which one of the primers would anneal to antigenomic RNA, while the other one would anneal to genomic HDV RNA (Example 6). Four hybrid RNAs were contemplated in which the 5' portion of the hairpin sequence (pode or antipode), including the loop, would be of genomic polarity, which would be followed (i.e., downstream) by an RNA sequence of antigenomic polarity, and vice versa (FIG. 5A).

Surprisingly, the only hybrid RNA product detected consisted of 5' sequences from the antigenomic pode RNA and 3' sequences from genomic RNA. This hybrid RNA product was also detected using primers of antigenomic polarity corresponding to a region upstream of the 5' end of the HDV small RNA and primers slightly downstream of the loop region (FIG. 5B, data not shown). The hybrid RNA was also detected independently of whether HDV replication resulted from DNA or RNA transfection, while the transfected DNA and RNA alone did not yield any hybrid PCR products (data not shown).

Figure 5:
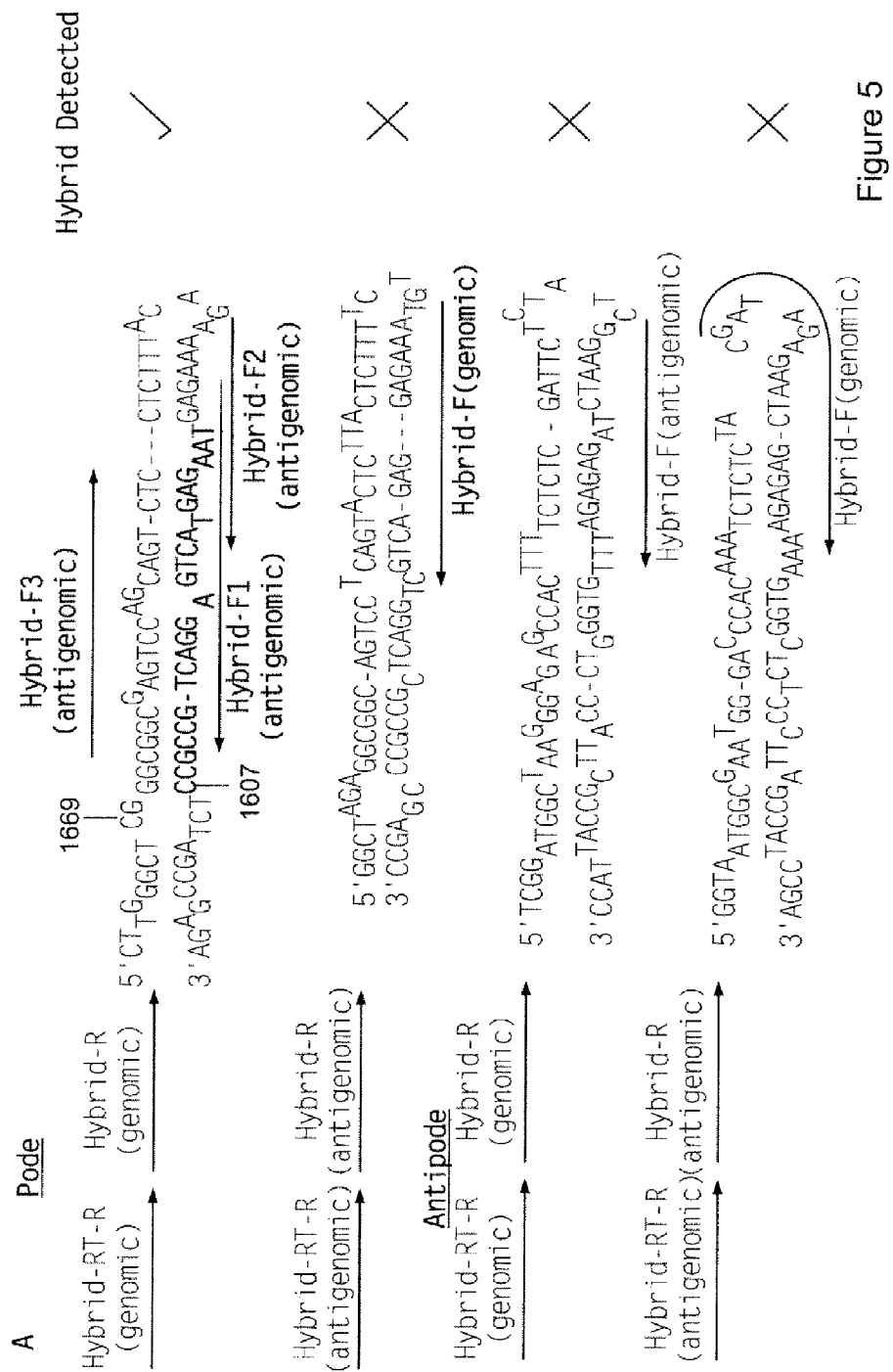
FIG. 5A shows the results of experiments performed to detect antigenomic-genomic HDV hybrid RNAs.
FIG. 5B shows the results of RT-PCR experiments based on the primer combinations shown in FIG. 5A.
FIG. 5C shows the sequence and relative mapping position in the genome of the cDNA sequence corresponding to the hybrid RNA with antigenomic sequence indicated in bold text and genomic sequence indicated in underlined text.
Figure 5:
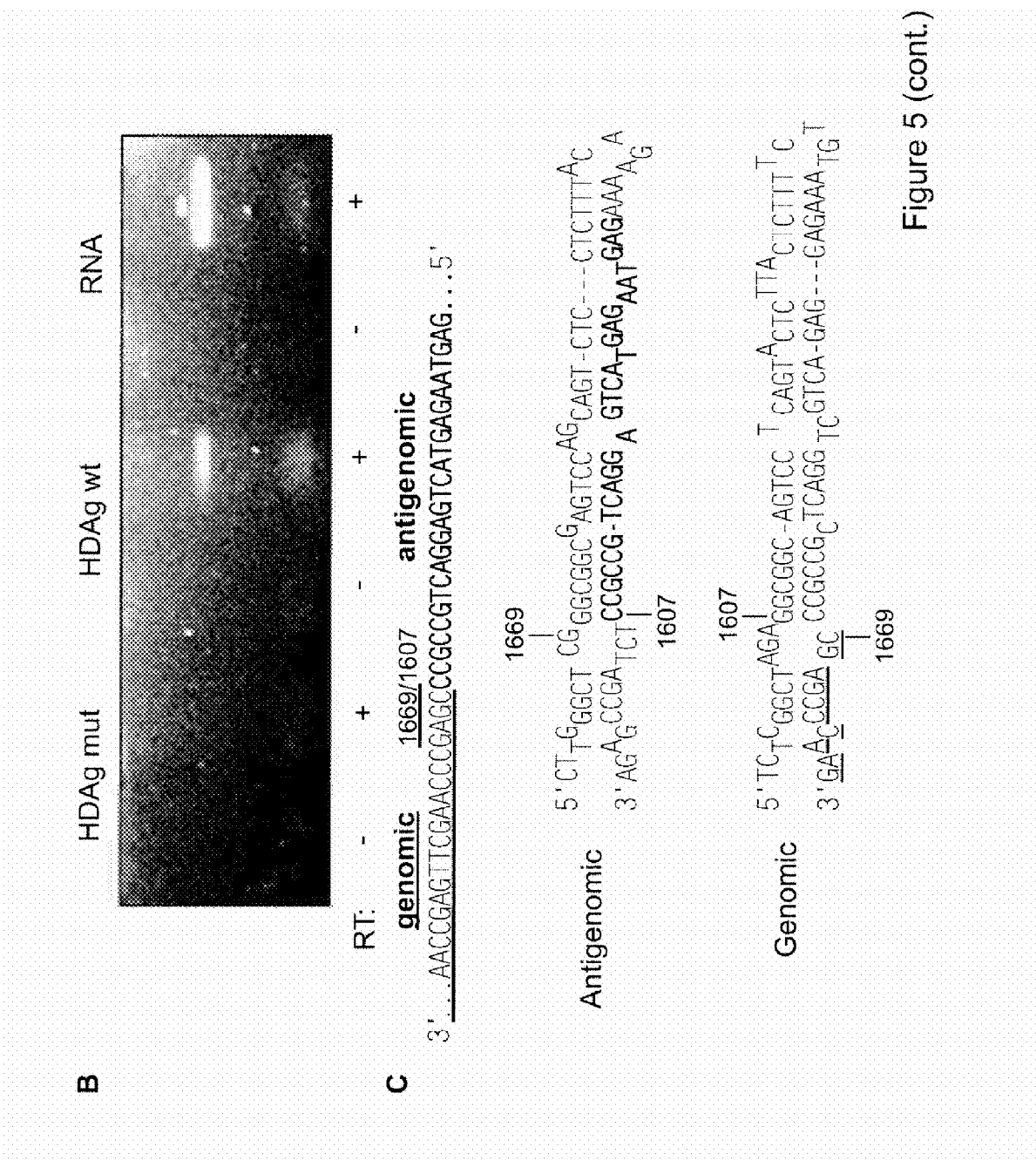

Multiple PCR products obtained using different antigenomic and genomic primer combinations were subjected to nucleotide sequence analysis to identify an antigenomic sequence that transitioned into genomic sequence just downstream of the conserved GC-rich box (FIG. 5C). The start position for the genomic portion of the sequence was immediately opposite the 3'-most antigenomic sequence in the secondary structure of the pode region, suggesting that it had been primed by the antigenomic 3' end at position 1,607, which corresponds to the 3' end of the HDV small RNA.

E. Discussion of the Results and Model for HDV RNA Replication

The HDV small RNA appears to represent a new type of stable small RNA that involved with HDV RNA-directed transcription. Unlike other classes of small RNAs previously discovered in eukaryotic organisms, such as microRNAs, siRNA, piRNAs, and RdRP-dependent small RNAs in RNAi-like pathways (Zamore, P. D. and Haley, B. *Science* 309: 1519-24 (2005); Kim, V. N. *Genes Dev.* 20:1993-7 (2006)), the ~23 nucleotide HDV small RNA does not appear to be a silencing RNA, consistent with the presence of a 5' cap structure, which is predicted to be incompatible with binding to the RiSC complex (Ma, J. B. et al. *Nature* 434:666-70 (2005)). Similarly, the 5' capped, 2'-' hydroxylated HCV small RNA seems unlikely to be a transient intermediate of de novo initiated transcription. Due to its discrete size and co-localisation with genomic HDV RNA, it is proposed that the HCV small RNA serves as a primer for RNA-directed Pol II transcription (rPol II), thereby representing a new class of small priming RNAs (spRNAs).

Figure 6:
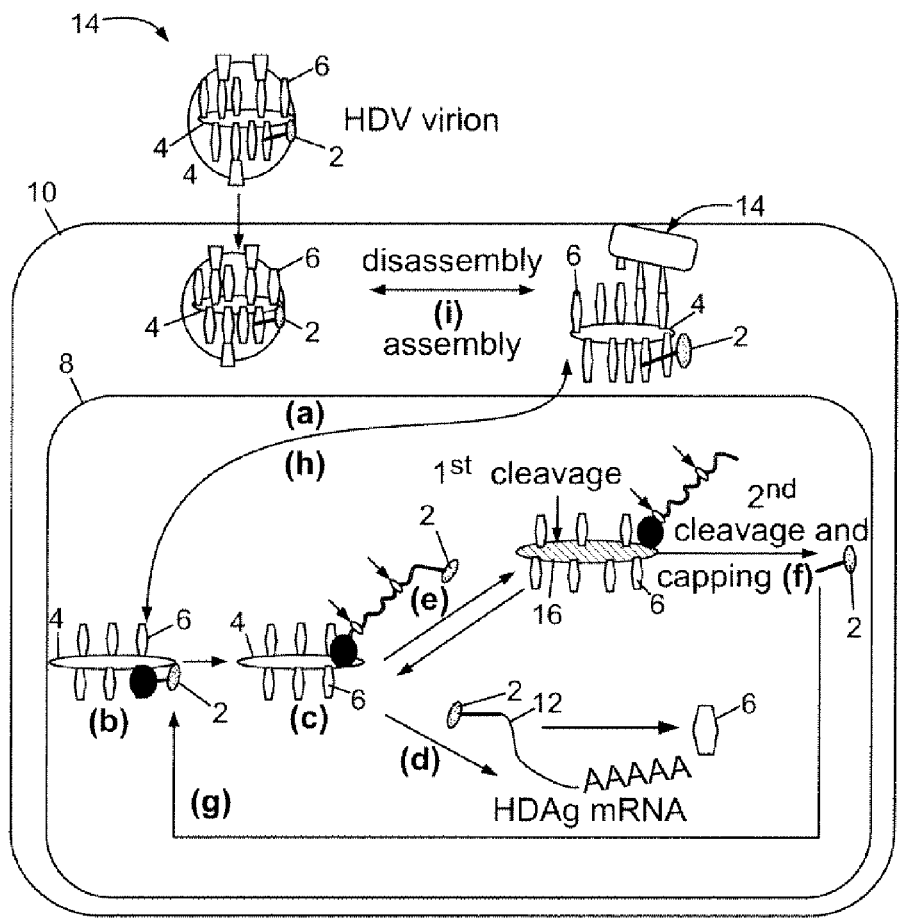
FIG. 6 shows a model for HDV replication.

Although the present compositions and methods are not limited to a particular theory, a model for HDV replication is proposed in FIG. 6. According to this model, the HDV small RNA (HDV spRNA) 2, together with genomic HDV RNA 4 and HDAg 6, is imported into the nucleus 8 of the host cell 10 as a ribonucleoprotein (RNP) following infection (a). Early de novo synthesis of HDAg mRNA 12 is important during virus infection (Sato, S. et al. *J. Virol.* 78:8120-34 (2004)) and may be facilitated by the presence of the capped HDV spRNA 2 in the infecting virus 14, which serves as a primer (b-c) for the rapid synthesis of HDAg mRNA 12 (*d*) by Pol II (not shown), in addition to the synthesis of downstream antigenomic RNA 16 (*e*).

Further according to the model, a single transcription initiation event would account for both the generation of HDAg mRNA 12 and antigenomic HDV RNA 16. The HDV spRNA may itself be generated by de novo synthesis from position 1,631/1,630, and may be similar to the RdRP-dependent secondary siRNAs found in *C. elegans*, which RNAs posses 5' di- and triphosphates, suggesting that each small RNA is the consequence of an unprimed transcription event (f) (Pak, J. and Fire, A. *Science* 315:241-4 (2007); Ruby, J. G. et al. *Cell* 127:1193-207 (2006); Sijen, T. *Science* 315:244-7 (2007)). The relationship between the 3' end of the spRNA 2 and the antigenomic-genomic hybrid RNA junction may be due to preferential localisation of Pol II to the antigenomic pode hairpin (Goodman, T. C. et al. *Nucleic Acids Res.* 12:6231-46 (1984)). However, the 5' end of the spRNA 2 could be generated by a second endonucleolytic cleavage event occurring at position 1,631, following a first cleavage at position 1,607, with capping occur via an unknown or non-canonical pathway. Antigenomic HDV RNA 16 (*g*) is exported together with genomic HDV RNA to the cytoplasm 10 (*h*) where it is packaged into a virion 14 (*i*) to serve as a primer in newly infected cells.

Overall, the results suggest that RNA-directed transcription occurs in mammalian cells and can be modulated using appropriately designed nucleic acid and small molecule compositions. Examples of these compositions and methods of their use are further described, below.

III. Compositions and Methods

The present compositions include short nucleic acids and small molecules that modulate the interaction between short RNAs, such as spRNAs, involved in RNA-directed transcription and their target viral or cellular nucleic acids. These short nucleic acids and small molecules are herein referred to as modulators of RNA-directed transcription, or, in proper context, "modulators." Modulators may increase or decrease the interaction between these short RNAs and their target sequences, in which case the may be referred to as "activators" or "inhibitors," respectively.

In some embodiments, the modulators are nucleic acid sequences that base-pair with the short RNAs, thereby preventing the short RNAs from base-pairing with their target sequence. Such nucleic acid sequences may be referred to as "inhibitor polynucleotides," which can be DNA, RNA, synthetic nucleic acid analogs, and the like, and may be coupled to other molecules to alter their properties or impart additional functionality. Exemplary inhibitor polynucleotides include a contiguous polynucleotide sequence that is substantially complementary (i.e., the reverse complement in terms of Watson-Crick nucleic acid base-pairing) to the particular short RNA, such as the HDV short RNA corresponding to SEQ ID NOs: 33 and 34. Such sequences may be called anti-sense nucleic acids. Exemplary sequences are provided, below.

| Sequence (5'→3') | SEQ ID NO: |
|---|---|
| gtcctcagtactcttact | 1 |
| ggcggcagtcctcagtactcttact | 35 |
| ggcggcagtcctcagtactctta | 36 |
| ggcggcagtcctcagtactctt | 37 |

In other embodiments, the modulators are nucleic acid sequences that base-pair with the target of the short RNAs, such as spRNAs, thereby activating RNA-directed transcription. Such nucleic acid sequences may be referred to as "activator polynucleotides," which can be DNA, RNA, synthetic nucleic acid analogs, and the like, and may be coupled to other molecules to alter their properties or impart additional functionality. Exemplary activator polynucleotides have the sequence of SEQ ID NOs: 33 or 34, or contiguous portions, thereof.

In some aspects, a modulator increases or decreases transcription by an RNA polymerase by binding to or altering the base-pairing between an spRNA or its target. In other aspects, a modulator increases or decreases the activity of the RNA polymerase or capping enzyme involved in biogenesis of an spRNA. In other aspects, a modulator of spRNA-directed transcription increases or decreases the downstream activity of an spRNA, such as, for example, a modulator of a transcription elongation factor (e.g., P-tef B)

In all cases, inhibitor and activator polynucleotides may include only a contiguous portion of such exemplary nucleic acids, and may be, e.g., 3 or more, 5 or more, 10 or more, 15 or more, 20 or more, or even 30 or more nucleotides in length. Additional inhibitor and activator polynucleotides have nucleotide sequences similar to those described, preferably with at least about 60% identity, at least about 70% identity, at least about 80% identity, or at least about 90% identity to the described sequences. Exemplary values are at least 81% identity, at least about 82% identity, at least about 83% identity, at least about 84% identity, at least about 85% identity, at least about 86% identity, at least about 87% identity, at least about 88% identity, at least about 89% identity, at least about 90% identity, at least about 91% identity, at least about 92% identity, at least about 93% identity, at least about 94% identity, at least about 95% identity, at least about 96% identity, at least about 97% identity, at least about 98% identity, and even at least about 99% identity.

Percent identity may be determined, for example, by comparing sequence information using the advanced BLAST computer program, including version 2.2.9, available from the National Institutes of Health. The BLAST program is based on the alignment method of Karlin and Altschul ((1990) *Proc. Natl. Acad. Sci. USA* 87:2264-68) and as discussed in Altschul et al. ((1990) *J. Mol. Biol.* 215:403-10; Karlin and Altschul (1993) Proc. Natl. Acad. Sci. USA 90:5873-77; and Altschul et al. (1997) *Nucleic Acids Res.* 25:3389-3402).

In other embodiments, the modulators are small molecules that alter or prevent base-pair between the short RNAs and their target sequence. Where such molecules prevent or reduce base-pairing, they may be referred to as "inhibitor molecules." Where such molecules increase or stabilize base-pairing, they may be referred to as "activator molecules,"

Inhibitor molecules and activator molecules can be nucleic acid binding molecules, including nucleic acid intercalation molecules, nucleotide and di-nucleotide analogs, antibodies or antibody fragments, and other naturally occurring or synthetic molecules. Such inhibitor molecules may be coupled to other molecules to alter their properties or impart additional functionality.

In other embodiments, the modulators are small molecules or nucleic acids that inhibit or activate the generation of the small priming RNA, thereby interfering or enhancing the function of the spRNA.

Compositions that include the present modulators may be delivered or administered to a mammalian subject/patient to produce a beneficial effect. In one embodiment, a composition is delivered or administered to reduce RNA-mediated transcription in virus infected cells, thereby treating or preventing a viral infection. In another embodiment, the pharmaceutical composition is delivered or administered to modulate cellular RNA-mediated transcription associated with diseases, disorders, or other conditions affecting mammalian subjects.

Use of the phrase "delivered or administered" is intended to convey that the modulator can be delivered to a cell via direct transfection, viral transduction, infection, or the like, or administered as a pharmaceutical composition or medicament in a convention dosage form, in which case the modulator is eventually delivered to cells.

A pharmaceutical composition that includes a modulator may be administered to a patient by a variety of routes. For example, such a composition may be administered parenterally, including intraperitoneally; intravenously; intraarterially; subcutaneously, or intramuscularly. The modulators may also be administered via a mucosal surface, including rectally, and intravaginally; intranasally; by inhalation, either orally or intranasally; orally, including sublingually; intraocularly and transdermally. Combinations of these routes of administration are also envisioned.

The modulators may also be administered in tablet form for sublingual administration, in a solution or emulsion. The modulators may also be mixed with a pharmaceutically-acceptable carrier or vehicle. In this manner, the modulators are used in the manufacture of a medicament treating various diseases and disorders. The vehicle may be a liquid, suitable, for example, for parenteral administration, including water, saline or other aqueous solution, or may be an oil or an aerosol. The vehicle may be selected for intravenous or intraarterial administration, and may include a sterile aqueous or non-aqueous solution that may include preservatives, bacteriostats, buffers and antioxidants known to the art. In the aerosol form, the modulator may be used as a powder, with properties including particle size, morphology and surface energy known to the art for optimal dispersability. In tablet form, a solid vehicle may include, for example, lactose, starch, carboxymethyl cellulose, dextrin, calcium phosphate, calcium carbonate, synthetic or natural calcium allocate, magnesium oxide, dry aluminum hydroxide, magnesium stearate, sodium bicarbonate, dry yeast or a combination thereof. The tablet preferably includes one or more agents which aid in oral dissolution. The modulators may also be administered in forms in which other similar drugs known in the art are administered, including patches, a bolus, time release formulations, and the like.

The modulators described herein may be administered for prolonged periods of time without causing desensitization of the patient to the therapeutic agent. That is, the modulators can be administered multiple times, or after a prolonged period of time including one, two or three or more days; one two, or three or more weeks or several months to a patient and will continue to cause an increase in the flow of blood in the respective blood vessel.

Suitable carriers, diluents and excipients are well known in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. Formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament). Some formulations may include carriers such as liposomes. Liposomal preparations include, but are not limited to, cytofectins, multilamellar vesicles and unilameliar vesicles. Excipients and formulations for parenteral and nonparenteral drug delivery are set forth in *Remington, The Science and Practice of Pharmacy* (2000).

The present methods also include identifying a therapeutic agent capable of inhibiting replication of HDV, for example, using the assays described herein to evaluate candidate agents.

The foregoing description and the following examples are not intended to be limiting. Further aspects and embodiments of the compositions and methods will be apparent to the skilled artisan in view of the present teachings.

All literature and similar materials cited in this application, including, but not limited to, patents, patent applications, articles, books, treatises, internet web pages and other publications cited in the present disclosure, regardless of the format of such literature and similar materials, are expressly incorporated by reference in their entirety for any purpose to the same extent as if each were individually indicated to be incorporated by reference. In the event that one or more of the incorporated literature and similar materials differs from or contradicts the present disclosure, including, but not limited to defined terms, term usage, described techniques, or the like, the present disclosure controls.

EXAMPLES

Example 1

Tissue Culture

To induce HDV replication by DNA transfection, Huh-7 and 293 cells were transfected with the plasmid pCMV3DCHDVx1_2ag using LIPOFECTAMINE® 2000 (Invitrogen), pCMV3DCHDVx1_2ag expresses 1.2× unit-length antigenomic HDV RNA and was kindly provided by Jeffrey Glenn of Stanford University. A first variant of this plasmid expressed a replication-deficient HDAg mutant produced by introducing a stop and frameshift mutation into pCMV3DCHDVx1_2ag downstream of the ATG start codon (i.e., atgagccggtccgagtcgaggaa→atgagccggtccgagtAgTagga; SEQ ID NO: 29 and 30, respectively). A second variant of this plasmid expressed only the small isoform of HDAg, and was obtained by mutating the ADAR editing site (i.e., cataggatatact→caATgATgatat; SEQ ID NO: 31 and 32, respectively). Note that only the small isoform of HDAg has been shown to be essential for HDV replication.

To induce HDV replication by RNA transfection, RNA transcribed in vitro using T7 polymerase and BamHI-linearized pCMV3DCHDVx1_2ag plasmid using the MMES-SAGE MMACHINE® kit (Ambion) and HDAg mRNA were transfected with Lipofectamine 2000. The template for the HDAg mRNA was obtained by XbaI linearization of pcDNA3 into which the HDAg ORF from pCMV3DCHDVx1_2ag was cloned downstream of the T7 promoter. RNA was harvested from cells 5 (293 cells) to 11 (Huh cells) days after transfection using Trizol reagent (Gibco) for obtaining total RNA, or the MIRVANA® kit (Ambion) for obtaining low-molecular weight RNA. Medium containing $5 \times 10^8$ HDV particles/ml was kindly provided by Robert Lanford (San Antonio). This medium was produced by co-transfecting the HDV expression vector pSVLD3 and an HBsAg expression vector into Huh-7 cells as published (Sureau, C. et al. *J. Virol.* 67:366-72 (1993)). 2.5 ml of medium was cleared by 2 min centrifugation at 4,000×g at 4° C. and RNA was isolated by adding 22.5 ml of Trizol reagent.

The results of the experiment are shown in FIG. C, with reference to the HDV RNA features shown in FIGS. 1A and 1B. An HDV-derived small RNA from the antigenomic pode was observed in both Huh-7 and 293 cells following the induction of HDV replication by DNA or RNA transfection. Lanes 1-3: Huh-7 cells, day 11. Lanes 4-7: 293 cells, day 6. Lane 1 and 5: Induction of HDV replication by transfecting a DNA encoding wt HDAg. Lane 2 and 6, Induction of HDV replication by transfecting a DNA encoding mutated HDAg. Lane 3: Induction of HDV replication by transfecting a DNA capable of expressing only the small form of HDAg. Lane 4: No induction/mock transfection. Lane 7: Induction of HDV replication by transfecting wt HDAg RNA. "MD: indicate the DNA marker. "MR" indicates the RNA marker. The results of the experiments are discussed in the text.

Example 2

Northern Blot Analysis

For the detection of small RNAs, ~5 ug of low-molecular weight RNA obtained using the MIRVANA® kit was separated by 15-20% urea-polyacrylamide gel electrophoresis, transferred onto Hybond-N (Amersham) nitrocellulose by semi-dry transfer, and hybridised to T4 PNK end-labelled oligonucleotide probes at 32° with PERFECTHYB PLUS® (Sigma) overnight. Blots were washed 3× with 6×SSC, 0.2% SDS (at 32° C., 34° C., and then 36° C.) and then once with 0.5×SSC, 0.1% SDS (at 42° C.) for 10 minutes each. Images were obtained by phosphorimaging. The size ladder used was the DECADE™ ladder (Ambion) or the 10 bp DNA Ladder (Invitrogen).

The following probes were used for the detection of viral RNAs. Probe 1 was used to detecting the HDV small RNA in the initial screen (FIGS. 1B and 1C).

preselected enzyme (below) at the indicated temperature for the indicated time. RNasin was not added where the preselected enzyme was terminator exonuclease.

| Enzyme | Amount |
| --- | --- |
| Tobacco acid pyrophosphatase (TAP) | 30 Units |
| Terminator exonuclease (TE) | 4 Units |
| Polynucleotide kinase (PNK) | 50 Units |
| RNA ligase | 100 Units |
| Antarctic phosphatase (AntP) | 25 Units |

| No. | Target | Sequence (5'→3') | SEQ ID NO: |
| --- | --- | --- | --- |
| 1 | HDV small RNA | gtcctcagtactcttact | 1 |
| 2 | antigenomic pode, bottom strand | ggcggcagtcctcagtactcttactctt | 2 |
| 3 | miR-15a1 | acaaaccattatgtgctgcta | 3 |
| 4 | let-7a1 | aactatacaacctactacctca | 4 |
| 5 | antigenomic antipode, top strand | gaatcgagagaaaagtggctct | 5 |
| 6 | antigenomic antipode, bottom strand | acccacaaatctctctctagattc | 6 |
| 7 | genomic antipode, top strand | gaatctagagagatttgtgggt | 7 |
| 8 | genomic antipode, bottom strand | agagccactttctctcgattc | 8 |
| 9 | antigenomic pode, top strand | taaagaggagactgctggactcgccgcc | 9 |
| 10 | genomic pode, top strand | aagagtaagagtactgaggactgccgcc | 10 |
| 11 | genomic pode, bottom strand | gcggcgagtccagcagtctcctctt | 11 |

For the detection of full-length HDV RNAs, 5 µg of Trizol-isolated total RNA was separated on 1% denaturing formaldehyde-agarose gels, transferred by wet-transfer onto Hybond-N (Amersham) nitrocellulose, and hybridised to either α-UTP labelled, T7 polymerase transcribed RNA from BamHI-linearised pCMV3DCHDVx1_2ag for the detection of genomic HDV RNA (68° C., PERFECTHYB PLUS®), or T4 PNK end-labelled probe ggcggcagtcctcagtactcttactctt (36° C., PERFECTHYB PLUS®; SEQ ID NO: 12).

Example 3

Analysis of Small RNA 3' and 5' Ends

β-elimination was performed as follows: RNA was dried in a speed-vac and dissolved in borax/boric acid buffer (0.06 M, pH 8.6). 2.5 µl of 200 mM sodium periodate was added and the mixture was incubated in the dark at room temperature for 60 minutes. 2 µl of glycerol was added followed by another 30-minute incubation. The reaction was concentrated in a speed-vac and dissolved in NaOH/borax/boric acid buffer (50 µl, 0.055 M, pH 9.5) and incubated at 45° C. for 90 minutes.

Enzyme treatments were performed by denaturing 10 µg RNA obtained using the MIRVANA® kit at 65° C. for 5 minutes, chilling the denatured RNA on ice for 2 minutes, and then adding enzyme buffer, RNasin (Promega), and finally a The results of these experiments are shown in FIGS. 3A-3D. As shown in FIG. 3A, the mobility of the HDV small RNA is increased following β-elimination. MiR-15a1, which is 2'-3' hydroxylated groups, serves as a positive control. "+β" indicates β-elimination, while "−β" indicates the untreated control. FIG. 3B shows the results of enzymatic analysis. Lane 1: mock-treated, includes HDV RNA. Lane 2: mock-treated, does not include HDV RNA. Lane 3: PNK-treated, includes HDV RNA. Lane 4: TAP-treated, includes HDV RNA. Lane 5: T4 RNA ligase-treated, includes HDV RNA. Lane 6: TE-treated, includes HDV RNA.

The size of the HDV small RNA was estimated to be ~23 nucleotides based on a comparison with the predominantly 22 nucleotide, 5'-phosphorylated, miR15-a1 RNA. FIG. 3C shows the results of incubating the HDV small RNA in the presence of antarctic phosphatise alone or followed by PNK. The enlarged image better shows the observed changes in gel mobility for the miR-15a1 RNA but not the HDV small RNA. Lane 1: mock-treated, includes HDV RNA. Lane 2: mock-treated, no HDV RNA. Lane 3: AntP-""treated, includes HDV RNA. Lane 4: AntP-treated followed by PNK-treated, includes HDV RNA. In FIGS. 3A-3C, Mir-15a1 RNA was detected after stripping the membrane and rehybridisation a primer for detecting the Mir-15a1 RNA to the same blot. "M" indicates the Decade RNA marker (Ambion).

Based on these and other results, the predicted structure of the HDV small RNA is shown in FIG. 3D, and discussed in the text.

Example 4

Nuclear-Cytoplasmic RNA Fractionation 293 cells from a 10 cm dish were washed with ice-cold PBS, scraped, and pelleted by centrifugation with 3,000×g for 2 minutes at 4° C. The pelleted cells were resuspended in 500 μl lysis buffer (0.14 M NaCl, 1.5 mM MgCl$_2$, 10 mM Tris-HCl pH 7.5, 0.5% NP40) and incubated on ice for 10 minutes. Nuclei were gently pelleted at 3,000×g for 2 minutes at 4° C. For cytoplasmic RNA, the supernatant was underlayered with an equal volume of lysis buffer containing 12% sucrose and subjected to further centifugation at 15,800×g for 10 minutes at 4° C. The supernatant (cytoplasmic fraction) was then twice acid phenol/chloroform extracted and then ethanol precipitated. For nuclear RNA, the pelleted nuclei were resuspended in 1 ml lysis buffer, lysis was confirmed by microscopy, and the nuclei were gently pelleted again at 3,000×g for 2 minutes at 4° C. RNA was then extracted from the pellet with Trizol reagent.

The results of the experiment are shown in FIGS. 4A-4C. The HDV small RNA was detected in both the nuclear and cytoplasmic RNA fraction (FIG. 4A) as were antigenomic and genomic HDV RNA (FIG. 4B). The primary genomic/antigenomic RNA species detected was the monomer, although higher molecular weight species (e.g., dimers, trimers, and the like) were also detected, as expected from rolling-circle replication. The identity of the samples used in FIGS. 4A and 4B are as follows: Lane 1: HDV replication was induced by transfecting DNA encoding a mutated HDAg. Lane 2: HDV replication was induced by transfecting DNA encoding a wt HDAg. Lane 3: No transfection (control).

FIG. 4C shows that the HDV small RNA is present in HDV virions/virus particles. Lane 1: HDV replication was induced by transfecting RNA (same RNA as in FIG. 3C). Lane 2: virion RNA was isolated from tissue culture media (~1.25× $10^9$ virus particles). "M" indicates the Decade RNA marker. "M*" indicates the DNA marker. The results of the experiments are discussed in the text.

Example 5

Primer Extension Assays

For primer extension assays, 5 pmol of primer extension oligonucleotide (i.e., PE-small or PE-NegControl) was end-labeled with 20 pmol of 6,000 Ci/mMole γ[$^{32}$P]ATP (PerkinElmer) using 20 Units of T4 PNK (NEB) for 1 hour. For the extension step, Superscript II Reverse Transcriptase (SS2RT, Invitrogen) was used. 5 μg of low molecular weight RNA obtained using the MIRVANA® kit was hybridized to 20,000 cpm of the end-labelled oligonucleotide primer by heating the nucleic acids to 70° C. for 5 minutes and then chilling the mixture on ice for 2 minutes. Following the addition of buffer, dNTP, and RNasin (Promega), the 40 ul reaction was incubated at 42° C. for 5 minutes, at which point 2 μl of SS2RT was added and the mixture incubated for 90 minutes. Termination was by heating the reaction for 5 minutes at 85° C., chilling on ice, and then adding 2 μl of 0.5 M EDTA (pH 8.0) and DNase-free RNase A to remove the RNA.

The following oligonucleotide primers were used:

| No. | Sequence (5'→3') | Comments | SEQ ID NO: |
|---|---|---|---|
| 1 | gcggcagtcctcagta | PE-small | 13 |
| 2 | gactcggaccggctcatct | PE-NegControl | 14 |

FIGS. 2A and 2B show the results of a mapping experiments using the indicated primers. The numbers in FIG. 2A (e.g., 20, 22, 25, 28, and 30) indicate the estimated sizes (i.e., lengths) of nucleotides. The "+[number]," (i.e., +6, and +17/18) indicates the amount of extension. The length of the unextended primer is 16 nucleotides. "HDV+" indicates DNA induction using a DNA encoding the wt HDAg. "HDV−" indicates DNA induction using a DNA encoding the mutated HDAg. As shown in FIG. 2B, the 5' end of the HDV small RNA maps predominantly to position 1631 (upright arrow). Arrows pointing to the left indicate known HDAg mRNA initiation sites (Hsieh, S. Y. et al. *J. Virol.* 64:3192-8 (1990); Modahl, L. E. and Lai, M. M. *J. Virol.* 72:5449-56 (1998); Gudima, S. et al. *J. Virol.* 73:6533-9 (1999)). The relative positions of the extension primers are indicated. "M" identifies the DNA marker lane. The results of the experiments are discussed in the text.

Example 6

RT-PCR Experiments to Identify
Antigenomic-Genomic Hybrid RNAs

The detection of antigenomic-genomic hybrid RNAs was by Superscript III Reverse Transcriptase (Invitrogen) reverse transcription followed by Taq2000 (Promega) PCR according to the manufacturers' instructions. Individual PCR products were cloned into pCR2.1 by Topo-TA cloning (Invitrogen) and sequenced. The following primers were used:

Antigenomic Pode-Genomic Hybrid

| No. | Target | Sequence (5'→3') | SEQ ID NO: |
|---|---|---|---|
| 1 | Hybrid-F1 | gagtaagagtactgaggactgcc | 15 |
| 2 | Hybrid-F2 | acagaaaagagtaagagtac | 16 |
| 3 | Hybrid-F3 | cggcgagtccagcagtctc | 17 |
| 4 | Hybrid-R | cccgcgtcctcgctcgga | 18 |
| 5 | Hybrid RT-R | tgacatcccctctcgggagc | 19 |

Genomic Pode-Antigenomic Hybrid

| No. | Target | Sequence (5'→3') | SEQ ID NO: |
|---|---|---|---|
| 1 | Hybrid-F | tctgtaaagaggagactgc | 20 |
| 2 | Hybrid-R | tacctccatctggtccgttc | 21 |
| 3 | Hybrid RT-R | cctcttcctaggtccggagt | 22 |

Antigenomic Antipode-Genomic Hybrid

| No. | Target      | Sequence (5'→3')             | SEQ ID NO: |
|-----|-------------|------------------------------|------------|
| 1   | Hybrid-F    | tctatcggaatctagagagatt       | 23         |
| 2   | Hybrid-R    | tcgacccagtgaataaagc          | 24         |
| 3   | Hybrid RT-R | atactcttcccagccgatcc         | 25         |

Genomic Antipode-Antigenomic Hybrid.

| No. | Target      | Sequence (5'→3')             | SEQ ID NO: |
|-----|-------------|------------------------------|------------|
| 1   | Hybrid-F    | cgatagagaatcgagagaa          | 26         |
| 2   | Hybrid-R    | gacccccttcgaaagtgac          | 27         |
| 3   | Hybrid RT-R | aaggggacgagtgaggcttat        | 28         |

Results obtained using the indicated primer/probe sets to detect the hybrid RNA in 293 cells are shown in FIGS. 5A-C. FIG. 5A shows the primer combinations used, the relative positions of the primers and their polarity, and whether a product was obtained in an RT-PCR reaction. The orientations of the primers are indicated by arrows and the HDV small RNA sequence is indicated in bold text.

FIG. 5B shows that antigenomic pode-genomic hybrid RNA was detected using the Hybrid-F1 primer following both RNA and DNA transfections. Antigenomic pode-genomic hybrid RNA was also detected using the Hybrid-F2 and Hybrid-F3 primers (data not shown). The lanes labelled "HDAg mut" indicate that HDV replication was induced by transfecting DNA encoding a mutated HDAg, and the subsequent RT-PCR reactions were performed in the absence (−) or presence (+) of the reverse transcriptase (RT). The lanes labelled "HDAg wt" indicate that HDV replication was induced by transfecting DNA encoding a wt HDAg, and the subsequent RT-PCR reactions were performed in the absence (−) or presence (+) of the reverse transcriptase (RT). The lanes labelled "RNA" indicate that HDV replication was induced by transfecting in vitro-transcribed antigenic HDV RNA, and the subsequent RT-PCR reactions were performed in the absence (−) or presence (+) of the reverse transcriptase (RT). The results of the experiments are discussed in the text.

Example 7

RNA Immunoprecipitation

For the immunoprecipitation of capped RNAs with the agarose-conjugated 2,2,7-trimethylguanosine monoclonal antibody [K121] (Abcam ab16769), 20 µl of K121 beads were incubated with 10 µg of low-molecular weight RNA by rotating for 3 hours to overnight at 40° C. in IP buffer: 0.01% (w/v) SDS, 1% (v/v) Triton-X-100, 1.2 mM EDTA pH 8.0, 16.7 mM Tris-HCl pH 8.0, 167 mM NaCl. The beads were washed three times with IP buffer.

What is claimed is:

1. An isolated small priming RNA (spRNA) molecule 18 to 35 nucleotides in length having a 5' cap and an ability to prime transcription by RNA polymerases, having a sequence with at least about 95% identity to SEQ ID NO: 33 or SEQ ID NO: 34.

2. The spRNA molecule of claim 1 having the sequence of SEQ ID NO: 33 or SEQ ID NO: 34.

3. A method for inhibiting replication of HDV, comprising providing a nucleic acid effective to bind to or inhibit the activity of the spRNA molecule of claim 1.

4. The method of claim 3, wherein the nucleic acid has the sequence selected from the group consisting of SEQ ID NO. 1 and SEQ ID NO. 35-37.

5. A method for identifying a therapeutic agent capable of inhibiting replication of HDV, comprising contacting the spRNA molecule of claim 1 with a candidate therapeutic agent and evaluating ability of the candidate agent to inhibit replication of HDV.

6. The method of claim 5, wherein said compound is selected from the group consisting of an antisense nucleic acid, an siRNA, an miRNA, a piRNA and an shRNA.

7. An antisense molecule or RNAi agent capable of hybridizing to the spRNA molecule of claim 1.

8. A system comprising the isolated spRNA molecule of claim 1, said system capable of replicating genomic HDV.

9. A nucleic acid which inhibits spRNA-primed transcription in a cell, wherein the spRNA is the spRNA of claim 1.

* * * * *

UNITED STATES PATENT AND TRADEMARK OFFICE
CERTIFICATE OF CORRECTION

| | | |
|---|---|---|
| PATENT NO. | : 8,034,922 B2 | Page 1 of 1 |
| APPLICATION NO. | : 12/545729 | |
| DATED | : October 11, 2011 | |
| INVENTOR(S) | : Mark A. Kay | |

It is certified that error appears in the above-identified patent and that said Letters Patent is hereby corrected as shown below:

In the Specification:

- Please replace lines 15-18 in column 1 as follows:

--This invention was made with government support under contracts AI071068 and DK078424 awarded by the National Institutes of Health. The government has certain rights in the invention.--

Signed and Sealed this
Third Day of May, 2016

Michelle K. Lee
*Director of the United States Patent and Trademark Office*